(12) United States Patent
Pecora

(10) Patent No.: US 9,734,291 B2
(45) Date of Patent: *Aug. 15, 2017

(54) CNA-GUIDED CARE FOR IMPROVING CLINICAL OUTCOMES AND DECREASING TOTAL COST OF CARE

(71) Applicant: Cota, Inc., New York, NY (US)

(72) Inventor: Andrew L. Pecora, Rumson, NJ (US)

(73) Assignee: COTA, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/351,099

(22) Filed: Nov. 14, 2016

(65) Prior Publication Data

US 2017/0061086 A1    Mar. 2, 2017

Related U.S. Application Data

(63) Continuation-in-part of application No. 15/233,577, filed on Aug. 10, 2016, now Pat. No. 9,646,135, which is a continuation-in-part of application No. 14/594,969, filed on Jan. 12, 2015, now Pat. No.
(Continued)

(51) Int. Cl.
| | |
|---|---|
| *G06Q 50/00* | (2012.01) |
| *G06Q 10/00* | (2012.01) |
| *G06F 19/00* | (2011.01) |
| *G06Q 10/06* | (2012.01) |

(Continued)

(52) U.S. Cl.
CPC .......... *G06F 19/328* (2013.01); *G06F 19/322* (2013.01); *G06F 19/324* (2013.01); *G06F 19/325* (2013.01); *G06F 19/345* (2013.01); *G06Q 10/0635* (2013.01); *G06Q 10/0637* (2013.01); *G06Q 10/1095* (2013.01); *G06Q 50/24* (2013.01)

(58) Field of Classification Search
CPC ............................ G06F 19/324; G06F 19/328
See application file for complete search history.

(56) References Cited

U.S. PATENT DOCUMENTS

| | | | |
|---|---|---|---|
| 6,699,193 | B2 | 3/2004 | Crutchfield |
| 7,774,377 | B2 | 8/2010 | Schoenberg |
| 8,019,552 | B2 | 9/2011 | Dai |

(Continued)

FOREIGN PATENT DOCUMENTS

WO    0042533 A1    7/2000

*Primary Examiner* — Luke Gilligan

(74) *Attorney, Agent, or Firm* — McCarter & English LLP

(57) ABSTRACT

CNA-guided care, which can improve clinical outcomes at a specific patient level and decrease total cost of care at the population level, has two faces. The first face, the enabling tool, allows a payer to transmit information identifying a health care service under consideration for a patient with a health condition whose health plan benefits cover the service and other payer-selected variables. In response, the payer receives information sufficient to establish that the medical service is an appropriate delivery or level of service allowing the payer to approve payment to a medical care provider for the service. The second face provides for communications that provide information sufficient for a complete medical evaluation and for assigning a CNA to the patient. The patient then can use the assigned CNA to select an optimal care plan and a medical professional based on patient-set criteria within the CNA.

30 Claims, 36 Drawing Sheets

Related U.S. Application Data 9,378,531, which is a continuation of application No. 14/507,640, filed on Oct. 6, 2014.

(60) Provisional application No. 61/888,418, filed on Oct. 8, 2013.

(51) Int. Cl.
*G06Q 10/10* (2012.01)
*G06Q 50/24* (2012.01)

(56) References Cited

U.S. PATENT DOCUMENTS

| | | |
|---|---|---|
| 8,731,648 B2 | 5/2014 | Bardy |
| 2008/0033894 A1 | 2/2008 | Steck et al. |
| 2008/0091472 A1 | 4/2008 | Hoppe |
| 2008/0312959 A1 | 12/2008 | Rose et al. |
| 2009/0204430 A1 | 8/2009 | Glikich |
| 2012/0029939 A1 | 2/2012 | Danielson et al. |
| 2012/0053425 A1* | 3/2012 | Michelson ............ G06F 19/24 600/300 |
| 2012/0130737 A1* | 5/2012 | Finizio ................ G06F 19/3487 705/2 |
| 2012/0166218 A1* | 6/2012 | Reiner ................ G06F 19/327 705/2 |
| 2012/0271612 A1* | 10/2012 | Barsoum ............ G06F 19/3431 703/11 |
| 2013/0226612 A1 | 8/2013 | Carmeli et al. |
| 2014/0006044 A1* | 1/2014 | Pradhan ............ G06F 19/3443 705/2 |
| 2014/0244277 A1 | 8/2014 | Krishna Rao et al. |

\* cited by examiner

KEY STAKEHOLDERS LOOKING FOR SOLUTIONS

DECISION SUPPORT

CNA-GUIDED CARE FOR IMPROVING CLINICAL OUTCOMES AND DECREASING TOTAL COST OF CARE

CROSS-REFERENCE TO RELATED APPLICATIONS

This application is a continuation in part of application Ser. No. 15/233,577 (filed Aug. 10, 2016), which is a continuation-in-part of U.S. application Ser. No. 14/594,969 (filed Jan. 12, 2015), entitled "Clinical outcome tracking and analysis," which issued as U.S. Pat. No. 9,378,531, which is a continuation of U.S. application Ser. No. 14/507,640 (filed Oct. 6, 2014), entitled "Clinical outcome tracking and analysis," which claims the benefit of priority to U.S. provisional application No. 61/888,418 (filed Oct. 8, 2013). The entire content of each of these applications is incorporated by reference herein.

FIELD

The present disclosure relates to CNA-guided care for improving clinical outcomes at the specific patient level and for decreasing total cost of care at the population level.

BACKGROUND

As the general population is living longer, most medical costs associated with the aging population are increasing. The costs associated with serious and chronic diseases, such as cancer, are growing in an unsustainable manner. For example, cancer costs are projected to be the highest growth area in healthcare spending without a commensurate improvement in outcomes. Approximately $125 billion was spent in 2010 on cancer care in the United States alone, and estimates are that approximately 15-30% of the spending can be categorized as a consequence of unnecessary or inappropriate care, where too little or too much care for an individual patient leads to less than optimal clinical outcomes and excessive expenses (hereinafter "Adverse Variance").

Under the current system, for every 100 people with a serious medical condition receiving care, there is on average a 20% rate of Adverse Variance, meaning that too little or too much care was delivered to an individual patient. Thus, a less than optimal clinical outcome occurs in 20% of the patients receiving care, resulting in an increase in total cost of care at the population level 100% of the time.

Conventional techniques to control costs, such as clinical pathways and disease management, are typically ineffective, and there are no quality alternatives that currently exist in the market today.

The current prior authorization infrastructure that enables a payer to determine that a medical service is a covered benefit under a patient's health plan is expensive and takes too much time, which can adversely affect clinical outcome by delaying necessary care.

As advancements in technology and medicine continue to occur, the science and clinical practice of caring for diseases (such as cancer, cardiovascular disease, pulmonary disease and behavioral health) are rapidly evolving. Often, medical professionals (e.g., oncologists) have a difficult time keeping up with these advancements. These advancements, such as next generation genetic sequencing, are typically complex and may present major issues for health plans and medical professionals. As a result, health plans will likely need more tools and support to manage their medical (e.g., oncology) business. Similarly, medical professionals (e.g., physicians) will need more decision support tools to practice best medicine and stay in business.

A clinical outcome tracking and analysis (COTA) module is a tool to, for example, enable medical professionals and/or other users to practice better medicine, better manage and locate specific information associated with a disease and/or patient, and facilitate improved control of cost.

The parameters of clinical outcome tracking and analysis include sorting, outcome tracking, Eastern Cooperative Oncology Group (ECOG) performance status; toxicity to therapy and cost of care. In one aspect, a method and system include the COTA module that receives, from a client device operated by a user, one or more parameters to sort a plurality of data records, and, in response to the receiving, sorts the data records based on the received parameters. A nodal address, indicating one or more variables, is applied to the sorted set of patient medical records to determine a clinically relevant set of patient medical records as the sorted set of patient medical records satisfying the one or more variables. The COTA module then analyzes the clinically relevant set of patient medical records and communicates at least a portion of the classified and sorted data records and the updated data records to a client device for display.

Each data record includes data associated with a disease and data associated with patients currently having the disease or patients who previously had the disease. The COTA module can receive the data from an electronic medical record (EMR), from a user, from a medical professional, from an expert, or from any other source.

The COTA module can enable the user to perform various analyses on one or more of the data records. For example, the COTA module can enable a comparison of data or of tracked outcomes between patients can identify a specific patient as a candidate for a specific treatment or drug, can communicate an analysis tool to the client device to facilitate analysis of, for instance, the classified and sorted data records or to enable comparison of Kaplan Meier curves, and can determine, based on the tracking, whether a specific doctor associated with a patient is treating the patient in accordance with treatment techniques of other doctors treating other (similar) patients.

The COTA module may also transmit an alert to the client device upon the occurrence of a trigger. A trigger may be, for example, at diagnosis, at progression, at dose change, at drug change, at toxicity, when trending towards variance from a desired outcome, and/or at a specific time.

The COTA module tracks consequences of treatment choices and reports on outcomes associated with the use of COTA Nodal Addresses (CNAs). It accounts for biological variance upfront by grouping patients in a patient population, which effectively removes biological variance as a factor in value of care, leaving treatment variance as a predominant factor in treatment outcome. The COTA module receives, collects, and records personal health information from each patient in the patient population in a database, and sorts the personal health information. Like personal health information is classified, and types of patients in the patient population are grouped based on the personal health information by generating and assigning a plurality of nodal addresses within the COTA module. Each CNA is represented as a discrete punctuated string of digits comprising a prefix, a middle, and a suffix that represent a set of preselected variables that partition the sorted and classified information into a clinically relevant set of health information. A plurality of CNAs reduces trillions of possible permutations to a reduced number of clinically meaningful permutations based on the discrete punctuated string of digits representing each nodal address that enable analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost; reduce processing requirements and time for processing to make real-time monitoring of medical provider performance efficient based on the discrete punctuated string of digits representing each nodal address and based on the reduction in permutations; and enable prediction of key points in time at which behavioral variance is likely to occur and interrupting treatment flow to avoid over-/under-utilization of care to prevent the behavioral variance.

The described invention provides CNA-guided care. CNA-guided care has two faces, which together, through the triad of a health care provider, a payer, and the patient suffering from a disease, enables value based care delivery in the United States through the application of CNAs.

The first face, the enabling tool, comprises interactions between a medical care provider, a computer containing a processor comprising a first COTA module, a first client device comprising a second COTA module that is communicatively linked to the first COTA via a network, and a payer. It enables a payer to transmit via the first client device comprising a second COTA module communicatively linked to the first COTA module of the processor, a communication over the network to the processor identifying a health care service under consideration for a patient whose health plan benefits cover the service; indicating that the service is for the purpose of diagnosing or treating a medical condition; and identifying variables selected by the payer. Upon receiving this communication from the payer, the first COTA module can transmit to the second COTA module information comprising (i) the clinical outcome data for each CNA, (ii) the adverse variance data for each medical provider at each CNA including both necessary care that is absent and unnecessary care contributing to the medical care provider's adverse variance for patients at each nodal address at key points in time during treatment; (iii) a cost report comprising cost data in real time for treating each patient in the patient population assigned to the CNA; and (iv) graphic analyses correlating one or more of (1) cost of care to clinical outcome; (2) incidence and severity of toxicity to cost of care and clinical outcome of care; and (3) therapy and quality of life. Based on this information, when the payer can establish at key points in time, (a) that the medical service is an appropriate delivery or level of service, considering potential benefits and harms to the patient; (b) that the medical service is effective in improving health outcome by improving clinical outcomes and reducing total cost of care; that the service is cost-effective for the medical condition being treated and the clinical outcome, compared to alternative health interventions or no intervention; and that the service follows generally accepted medical practice, the payer can approve payment to the medical care provider for the medical service for the patient.

From the payer's vantage point, this enabling tool can be effective to eliminate precertification for testing, diagnostics, and therapeutic choices; eliminate prior authorization; and eliminate the need for referrals. From the medical care provider's vantage point, it reduces the time necessary to pay the provider for healthcare. Accordingly, the enabling tool enables healthcare to optimize fee for service based reimbursement and to move from fee for services to risk-based care reimbursement (for example by bundling services), The second face of CNA-guided healthcare comprises interactions between the computer containing the processor comprising the first COTA module, a second client device comprising a third COTA module that is communicatively linked to the first COTA module via a network, and the patient. Through a series of communications between the first COTA module and the patient, CNA-guided healthcare, first, provides the patient with information sufficient for the patient to get a complete medical evaluation of his/her condition and for the first COTA module to assign a CNA to the patient; second, using the CNA, it shows the patient treatment options based on geography, clinical outcome, cost and other patient-set criteria that enable the patient to select care optimized to avoid adverse variance; third it shows the patient health care providers in his/her area who follow CNA guided care that have the best outcomes at an acceptable cost of care.

SUMMARY OF THE INVENTION

The described invention provides a method, a system and non-transitory computer readable medium storing computer program instructions that when executed on a processor cause the first COTA module to perform operations that use CNA-guided care to improve clinical outcomes at a specific patient level and to decrease total cost of care at the population level.

According to one aspect, the described invention provides a method for improving clinical outcomes at a specific patient level and for decreasing total cost of care at a population level comprising: A. interactions between a medical care provider, a computer containing a processor comprising a first clinical outcome tracking and analysis module, a first client device comprising a second clinical outcome tracking and analysis module that is communicatively linked to the first clinical outcome tracking and analysis module via a network, and a payer; and B interactions between the computer containing the processor comprising a first clinical outcome tracking and analysis module, a second client device comprising a third clinical outcome tracking and analysis module communicatively linked to the first clinical outcome tracking and analysis module via the network, and a patient, the computer containing the processor comprising the first clinical outcome tracking and analysis module executing on the processor comprising the first clinical outcome tracking and analysis module, steps comprising: (a) accounting for biological variance upfront by grouping patients in a patient population, thereby effectively removing biological variance as a factor in value of care, and leaving treatment variance as a predominant factor in treatment outcome by: (i) receiving, collecting and recording in a database personal health information from each patient in the patient population, the personal health information comprising each parameter that characterizes each patient in the patient population and information that impacts survival, prognosis, or treatment based on the latest scientific knowledge or medical guidelines. (ii) sorting the personal health information for each patient in the patient population using a sorting filter to provide a sorted set of personal health information for that population, and to identify patients satisfying each parameter in the patient population; (iii) classifying like personal health information, and grouping types of patients in the patient population based on the personal health information associated with the patient population by generating and assigning a plurality of Clinical outcome tracking and analysis Nodal Addresses (CNAs) within the first clinical outcome tracking and analysis module, wherein said generating and assigning said plurality of nodal addresses comprises: (1) representing each CNA as a discrete punctuated string of digits comprising a prefix, a middle and a suffix that represent a set of preselected variables that partition the sorted and classified information into a clinically relevant set of health information; (2) reducing trillions of possible permutations to a reduced number of clinically meaningful permutations based on the discrete punctuated string of digits representing each CNA that enable analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost; (3) reducing processing requirements and time for processing to make real-time monitoring of medical provider performance efficient based on the discrete punctuated string of digits representing each CNA and based on the reduction in permutations; and (4) enabling prediction of key points in time at which behavioral variance is likely to occur and interrupting treatment flow to avoid over-/under-utilization of care to prevent the behavioral variance; (iv) measuring clinical outcome for each CNA by: analyzing the clinically relevant set of personal health information for the subset of the patient population for one or more patients in the subset of the patient population; and (v) measuring behavioral variance for each medical care provider of each patient in the patient population assigned to each CNA by comparing differences between one medical care provider and another medical care provider in treating, testing, following up, complying with prescribed medicines, and cost for each patient in the patient population assigned to each CNA; (b) upon receiving communications from the payer via the first client device comprising the second clinical outcome tracking and analysis module identifying a health care service under consideration for the patient whose health plan benefits cover the medical service and variables selected by the payer, transmitting to the second clinical outcome tracking and analysis module information comprising, (1') the clinical outcome data for each CNA in (iv), (2') the behavioral variance data for each medical provider at each CNA in (v); (3') a cost report comprising cost data in real time for treating each patient in the patient population assigned to the CNA in (iii); and (4') one or more graphic analyses correlating cost of care to clinical outcome; wherein the information is sufficient for the payer to establish at the key points in time, (a') that the medical service is an appropriate delivery or level of service, considering potential benefits and harms to the patient; (b') that the medical service is effective in improving health outcome by improving clinical outcomes and reducing total cost of care; (c') that the service is cost-effective for the medical condition being treated and the clinical outcome, compared to alternative health interventions or no intervention; and (d') that the service follows generally accepted medical practice, and for the payer to approve payment to the medical care provider for the medical service; (c) upon exchanging a series of communications with the patient via the second client device comprising the third clinical outcome tracking and analysis module, providing information sufficient for a complete medical evaluation of the patient and for assigning a CNA to the patient, and using the CNA to determine an optimal level of care with a reduced risk of adverse variance; and to select a health care provider and a desired level of CNA-guided care, the series of communications comprising: (i") in response to a first communication from the patient reporting a health concern to the processor of the computer server comprising the first clinical outcome tracking and analysis module, sending to the second client device comprising the third clinical outcome tracking and analysis module in reply a second communication containing list of tests needed to diagnose the health concern as a medical condition; (ii") in response to a third communication from the patient containing results of the tests needed to diagnose the health concern in (i"), sending to the second client device comprising the third clinical outcome and analysis module in reply a fourth communication containing a diagnosis of the medical condition and a list of additional tests needed for further classifying the medical condition; (iii") in response to a fifth communication from the patient containing the results of the additional tests in (i"), based on the results of the tests, the diagnosis in (ii"), and the list of additional tests in (ii"), (a") assigning, a CNA to the patient from the plurality of CNAs available in a(iii), the assigned CNA containing the clinically relevant set of health information for the patient; and (b") transmitting to the second client device comprising the third clinical outcome tracking module a sixth communication comprising: (1") the assigned CNA; and (2") a geographically organized list of medical professionals treating patients within the assigned CNA, wherein the list of medical professionals is classified by one or more of geography, clinical outcome or cost; (iv") in response to a seventh communication from the patient selecting an optimal care plan comprising a reduced risk of adverse variance and a medical professional that meets at least one or more of geographical, cost, and outcome needs of the patient communicatively linking to a computing device comprising a third clinical outcome tracking and analysis module at the selected medical professional's office to facilitate the scheduling of an appointment of the patient with the selected medical professional.

In some embodiments of the method, (a) the parameters of sorting in (a)(ii) comprise one or more of: sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers, and cost of care; or (b) the set of preselected variables in (a)(iii)(1) includes a disease-specific clinical molecular phenotype, wherein the string of digits representing the phenotype is determined based on a directed graph; or (c) the key points in time in step (a)(iii)(4) and step (b)(i')(4') include one or more of at diagnosis, at progression, at dose change; at drug change; upon toxicity, and trending towards variance from desired outcome; or (d) the correlating cost of care to clinical outcome step in (b)(1')(4') comprises correlating one or more of incidence of toxicity, severity of toxicity; therapy; and quality of life to cost of care and outcome of care; or (e) the receiving of the transmission from the client device in (b) or (c) is via a human user or a technical process; or (f) the assigned CNA in (c)(iii")(b")(1") is associated with one or more bundles of predetermined patient care services for treatment of the condition; or (g) the clinical outcome in (c)(iii")(b")(2") comprises one or more of: therapeutic agent received, delivered dose intensity, dose interval, dose duration, quality of life metrics, toxicity to therapy, progression free survival, overall survival, response metrics, and death; or (h) the list of medical professionals in step (c)(iii")(b")(2") is visually classified by clinical outcome.

In some embodiments, the one or more bundles of predetermined patient care services provides a predetermined course of treatment, cost certainty for treatment of the condition, or both.

In some embodiments, the method further comprises identifying the best clinical outcome at the lowest cost of care at the CNA by ranking both clinical outcome and cost of care in the one or more bundles of predetermined patient care services.

In some embodiments, visual classification of the list of medical professionals by clinical outcome comprises: (a) green signifying a better than average clinical outcome; (b) yellow signifying an average clinical outcome; and (c) red signifying a poorer than average clinical outcome.

In some embodiments, the method further comprises, with permission from the patient and the selected medical professional: transmitting the personal health information of the patient from the first clinical outcome tracking and analysis module, to a computing device comprising a fourth clinical outcome tracking and analysis module at the selected medical professional's office.

In some embodiments, the behavioral variance data for each medical provider at each CNA in (c) includes both necessary care that is absent and unnecessary care contributing to the medical care provider's adverse variance for patients at each CNA at the key points in time during treatment.

In some embodiments, the method further comprises in step (d) indicating that the service is for the purpose of diagnosing or treating a medical condition.

In some embodiments, the cost report contains: a comparison between physician and average cost per revenue; or hospital contribution margin in dollars and percent comparisons; or hospital average revenue per patient; or hospital average cost per patient; or average cost per case for each physician, weight peer average; or average cost of imaging, lab work, evaluation and management; or pharmaceuticals, medical supplies and other expenses for each physician; or a combination thereof.

In some embodiments, the variables selected by the payer include variables that identify certain attributes of the personal health information as a desired set of characteristics; one or more attributes added by the payer to the personal health information to identify the personal health information of each patient as being on an equal level of importance to other health information in the patient population database, or both.

According to another aspect, the described invention provides a system for improving clinical outcomes at a specific patient level and for decreasing total cost of care at a population level comprising: (A) a processor of a computer server comprising: a database comprising personal health information and data for a population of human subjects; a first clinical outcome tracking and analysis module communicatively linked to the database and a network; and a memory to store computer program instructions; (B) a first client device comprising a processing unit; a memory, and a second clinical outcome tracking and analysis module communicatively linked to the first clinical outcome tracking and analysis module of the processor of the computer server; and (C) a second client device comprising a processing unit, a memory, and a third clinical outcome tracking and analysis module communicatively linked to the first clinical outcome tracking and analysis module of the processor of the computer server; the computer program instructions of (A), when executed on the processor causing the first clinical outcome tracking and analysis module to perform operations comprising: (a) accounting for biological variance upfront by grouping patients in a patient population, thereby effectively removing biological variance as a factor in value of care, and leaving treatment variance as a predominant factor in treatment outcome by: (i) receiving, collecting and recording in a database personal health information from each patient in the patient population, the personal health information comprising each parameter that characterizes each patient in the patient population and information that impacts survival, prognosis, or treatment based on the latest scientific knowledge or medical guidelines; (ii) sorting the personal health information for each patient in the patient population using a sorting filter to provide a sorted set of personal health information for that population, and to identify patients satisfying each parameter in the patient population; (iii) classifying like personal health information, and grouping types of patients in the patient population based on the personal health information associated with the patient population by generating and assigning a plurality of Clinical outcome tracking and analysis Nodal Addresses (CNAs) within the first clinical outcome tracking and analysis module, wherein said generating and assigning said plurality of CNAs comprises: (1) representing each CNA as a discrete punctuated string of digits comprising a prefix, a middle and a suffix that represent a set of preselected variables that partition the sorted and classified information into a clinically relevant set of health information; (2) reducing trillions of possible permutations to a reduced number of clinically meaningful permutations based on the discrete punctuated string of digits representing each CNA that enable analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost; (3) reducing processing requirements and time for processing to make real-time monitoring of medical provider performance efficient based on the discrete punctuated string of digits representing each CNA and based on the reduction in permutations; and (4) enabling prediction of key points in time at which behavioral variance is likely to occur and interrupting treatment flow to avoid over-/under-utilization of care to prevent the behavioral variance; (iv) measuring clinical outcome for each CNA by: analyzing the clinically relevant set of personal health information for the subset of the patient population for one or more patients in the subset of the patient population; and (v) measuring behavioral variance for each medical care provider of each patient in the patient population assigned to each CNA by comparing differences between one medical care provider and another medical care provider in treating, testing, following up, complying with prescribed medicines, and cost for each patient in the patient population assigned to each CNA; (b) upon receiving communications from the payer via the first client device comprising the second clinical outcome tracking and analysis module identifying a health care service under consideration for the patient whose health plan benefits cover the medical service and variables selected by the payer, transmitting to the second clinical outcome tracking and analysis module information comprising: (1') the clinical outcome data for each CNA in (iv); (2') the behavioral variance data for each medical provider at each CNA in (v); (3') a cost report comprising cost data in real time for treating each patient in the patient population assigned to the CNA in (iii); and (4') one or more graphic analyses correlating cost of care to clinical outcome;

wherein the information is sufficient for the payer to establish at the key points in time, (a') that the medical service is an appropriate delivery or level of service, considering potential benefits and harms to the patient; (b') that the medical service is effective in improving health outcome by improving clinical outcomes and reducing total cost of care; (c') that the service is cost-effective for the medical condition being treated and the clinical outcome, compared to alternative health interventions or no intervention; and (d') that the service follows generally accepted medical practice, and for the payer to approve payment to the medical care provider for the medical service; (c) upon exchanging a series of communications with the patient via the second client device comprising the third clinical outcome tracking and analysis module, providing information sufficient for a complete medical evaluation of the patient and for assigning a CNA to the patient, and using the CNA to determine an optimal level of care with a reduced risk of adverse variance; and to select a health care provider and a desired level of CNA-guided care, the series of communications comprising: (i") in response to a first communication from the patient reporting a health concern to the processor of the computer server comprising the first clinical outcome tracking and analysis module, sending to the second client device comprising the third clinical outcome tracking and analysis module in reply a second communication containing list of tests needed to diagnose the health concern as a medical condition; (ii") in response to a third communication from the patient containing results of the tests needed to diagnose the health concern in (i"), sending to the second client device comprising the third clinical outcome and analysis module in reply a fourth communication containing a diagnosis of the medical condition and a list of additional tests needed for further classifying the medical condition; (iii") in response to a fifth communication from the patient containing the results of the additional tests in (i"), based on the results of the tests, the diagnosis in (ii"), and the list of additional tests in (ii"), (a") assigning, a CNA to the patient from the plurality of CNAs available in a(iii), the assigned CNA containing the clinically relevant set of health information for the patient; and (b") transmitting to the second client device comprising the third clinical outcome tracking module a sixth communication comprising: (1") the assigned CNA; and (2") a geographically organized list of medical professionals treating patients within the assigned CNA, wherein the list of medical professionals is classified by one or more of geography, clinical outcome or cost; (iv") in response to a seventh communication from the patient selecting an optimal care plan with a reduced risk of adverse variance and a medical professional that meets at least one or more of geographical, cost, and outcome needs of the patient, communicatively linking to a computing device comprising a third clinical outcome tracking and analysis module at the selected medical professional's office to facilitate the scheduling of an appointment of the patient with the selected medical professional.

In some embodiments, (a) the parameters of sorting in (a)(ii) comprise one or more of: sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers, and cost of care; or (b) the set of preselected variables in (a)(iii)(1) includes a disease-specific clinical molecular phenotype, wherein the string of digits representing the phenotype is determined based on a directed graph; or (c) the key points in time in step (a)(iii)(4) and step (b)(i')(4') include one or more of at diagnosis, at progression, at dose change; at drug change; upon toxicity, and trending towards variance from desired outcome; or (d) the correlating cost of care to clinical outcome step in (b)(1')(4') comprises correlating one or more of incidence of toxicity, severity of toxicity; therapy; and quality of life to cost of care and outcome of care; or (e) the receiving of the transmission from the client device in (b) or (c) is via a human user or a technical process; or (f) the assigned CNA in (c)(iii")(b")(1") is associated with one or more bundles of predetermined patient care services for treatment of the condition; or (g) the clinical outcome in (c)(iii")(b")(2") comprises one or more of: therapeutic agent received, delivered dose intensity, dose interval, dose duration, quality of life metrics, toxicity to therapy, progression free survival, overall survival, response metrics, and death; or (h) the list of medical professionals in step (c)(iii")(b")(2") is visually classified by clinical outcome.

In some embodiments, the one or more bundles of predetermined patient care services provides a predetermined course of treatment, cost certainty for treatment of the condition, or both.

In some embodiments, the system further comprises identifying the best clinical outcome at the lowest cost of care at the assigned CNA by ranking both clinical outcome and cost of care in the one or more bundles of predetermined patient care services.

In some embodiments, the visual classification of the list of medical professionals by clinical outcome comprises: (a) green signifying a better than average clinical outcome; (b) yellow signifying an average clinical outcome; and (c) red signifying a poorer than average clinical outcome.

In some embodiments, the system further comprises, with permission from the patient and the selected medical professional, transmitting the personal health information of the patient from the first clinical outcome tracking and analysis module, to a computing device comprising a fourth clinical outcome tracking and analysis module at the selected medical professional's office.

In some embodiments, the behavioral variance data for each medical provider at each CNA in (c) includes both necessary care that is absent and unnecessary care contributing to the medical care provider's adverse variance for patients at each CNA at the key points in time during treatment.

In some embodiments, the system further comprises further comprises indicating that the service is for the purpose of diagnosing or treating a medical condition.

In some embodiments, the cost report contains: a comparison between physician and average cost per revenue; or hospital contribution margin in dollars and percent comparisons; or hospital average revenue per patient; or hospital average cost per patient; or average cost per case for each physician, weight peer average; or average cost of imaging, lab work, evaluation and management; or pharmaceuticals, medical supplies and other expenses for each physician; or a combination thereof.

In some embodiments, the variables selected by the payer include variables that identify certain attributes of the personal health information as a desired set of characteristics; one or more attributes added by the payer to the personal health information to identify the personal health information of each patient as being on an equal level of importance to other health information in the patient population database, or both.

According to another aspect, the described invention provides a non-transitory computer readable medium storing computer program instructions for facilitating interactions (A) between a medical care provider, a computer containing a processor comprising a first clinical outcome tracking and analysis module, a first client device comprising a second clinical outcome tracking and analysis module communicatively linked to the first clinical outcome tracking and analysis module via a network, and a payer; and (B) between the computer containing the processor comprising a first clinical outcome tracking and analysis module, a second client device comprising a third clinical outcome tracking and analysis module communicatively linked to the first clinical outcome tracking and analysis module via the network, and a patient, which, when executed on the processor comprising the first clinical outcome tracking and analysis module, causes the first clinical outcome and tracking module to perform operations comprising: (a) accounting for biological variance upfront by grouping patients in a patient population, thereby effectively removing biological variance as a factor in value of care, and leaving treatment variance as a predominant factor in treatment outcome by: (i) receiving, collecting and recording in a database personal health information from each patient in the patient population, the personal health information comprising each parameter that characterizes each patient in the patient population and information that impacts survival, prognosis, or treatment based on the latest scientific knowledge or medical guidelines; (ii) sorting the personal health information for each patient in the patient population using a sorting filter to provide a sorted set of personal health information for that population, and to identify patients satisfying each parameter in the patient population; (iii) classifying like personal health information, and grouping types of patients in the patient population based on the personal health information associated with the patient population by generating and assigning a plurality of Clinical outcome tracking and analysis Nodal Addresses (CNAs) within the first clinical outcome tracking and analysis module, wherein said generating and assigning said plurality of nodal addresses comprises: (1) representing each CNA as a discrete punctuated string of digits comprising a prefix, a middle and a suffix that represent a set of preselected variables that partition the sorted and classified information into a clinically relevant set of health information; (2) reducing trillions of possible permutations to a reduced number of clinically meaningful permutations based on the discrete punctuated string of digits representing each CNA that enable analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost; (3) reducing processing requirements and time for processing to make real-time monitoring of medical provider performance efficient based on the discrete punctuated string of digits representing each CNA and based on the reduction in permutations; and (4) enabling prediction of key points in time at which behavioral variance is likely to occur and interrupting treatment flow to avoid over-/under-utilization of care to prevent the behavioral variance; (iv) measuring clinical outcome for each nodal address by: analyzing the clinically relevant set of personal health information for the subset of the patient population for one or more patients in the subset of the patient population; and (v) measuring behavioral variance for each medical care provider of each patient in the patient population assigned to each CNA by comparing differences between one medical care provider and another medical care provider in treating, testing, following up, complying with prescribed medicines, and cost for each patient in the patient population assigned to each CNA; (b) upon receiving communications from the payer via the first client device comprising the second clinical outcome tracking and analysis module identifying a health care service under consideration for the patient whose health plan benefits cover the medical service and variables selected by the payer, transmitting to the second clinical outcome tracking and analysis module information comprising: (1') the clinical outcome data for each CNA in (iv); (2') the behavioral variance data for each medical provider at each CNA in (v); (3') a cost report comprising cost data in real time for treating each patient in the patient population assigned to the CNA in (iii); and (4') one or more graphic analyses correlating cost of care to clinical outcome; wherein the information is sufficient for the payer to establish at the key points in time, (a') that the medical service is an appropriate delivery or level of service, considering potential benefits and harms to the patient; (b') that the medical service is effective in improving health outcome by improving clinical outcomes and reducing total cost of care; (c') that the service is cost-effective for the medical condition being treated and the clinical outcome, compared to alternative health interventions or no intervention; and (d') that the service follows generally accepted medical practice, and for the payer to approve payment to the medical care provider for the medical service; (c) upon exchanging a series of communications with the patient via the second client device comprising the third clinical outcome tracking and analysis module, providing information sufficient for a complete medical evaluation of the patient and for assigning a CNA to the patient, and using the CNA to determine an optimal level of care with a reduced risk of adverse variance; and to select a health care provider and a desired level of CNA-guided care, the series of communications comprising: (i") in response to a first communication from the patient reporting a health concern to the processor of the computer server comprising the first clinical outcome tracking and analysis module, sending to the second client device comprising the third clinical outcome tracking and analysis module in reply a second communication containing list of tests needed to diagnose the health concern as a medical condition; (ii") in response to a third communication from the patient containing results of the tests needed to diagnose the health concern in (i"), sending to the second client device comprising the third clinical outcome and analysis module in reply a fourth communication containing a diagnosis of the medical condition and a list of additional tests needed for further classifying the medical condition; (iii") in response to a fifth communication from the patient containing the results of the additional tests in (i"), based on the results of the tests, the diagnosis in (ii"), and the list of additional tests in (ii"): (a") assigning, a CNA to the patient from the plurality of CNAs available in a(iii), the assigned CNA containing the clinically relevant set of health information for the patient; and (b") transmitting to the second client device comprising the third clinical outcome tracking module a sixth communication comprising: (1") the assigned CNA; and (2") a geographically organized list of medical professionals treating patients within the assigned nodal address, wherein the list of medical professionals is classified by one or more of geography, clinical outcome or cost; (iv") in response to a seventh communication from the patient selecting an optimal care plan with a reduced risk of adverse variance and a medical professional that meets at least one or more of geographical, cost, and outcome needs of the patient communicatively linking to a computing device comprising a third clinical outcome tracking and analysis module at the selected medical professional's office to facilitate the scheduling of an appointment of the patient with the selected medical professional.

In some embodiments, (a) the parameters of sorting in (a)(ii) comprise one or more of: sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers, and cost of care; or (b) the set of preselected variables in (a)(iii)(1) includes a disease-specific clinical molecular phenotype, wherein the string of digits representing the phenotype is determined based on a directed graph; or (c) the key points in time in step (a)(iii)(4) and step (b)(i')(4') include one or more of at diagnosis, at progression, at dose change; at drug change; upon toxicity, and trending towards variance from desired outcome; or (d) the correlating cost of care to clinical outcome step in (b)(1')(4') comprises correlating one or more of incidence of toxicity, severity of toxicity; therapy; and quality of life to cost of care and outcome of care; or (e) the receiving of the transmission from the client device in (b) or (c) is via a human user or a technical process; or (f) the assigned CNA in (c)(iii")(b")(1") is associated with one or more bundles of predetermined patient care services for treatment of the condition; or (g) the clinical outcome in (c)(iii")(b")(2") comprises one or more of: therapeutic agent received, delivered dose intensity, dose interval, dose duration, quality of life metrics, toxicity to therapy, progression free survival, overall survival, response metrics, and death; or (h) the list of medical professionals in step (c)(iii")(b")(2") is visually classified by clinical outcome.

In some embodiments, the one or more bundles of predetermined patient care services provides a predetermined course of treatment, cost certainty for treatment of the condition, or both.

In some embodiments, the non-transitory computer readable medium further comprises identifying the best clinical outcome at the lowest cost of care at the assigned CNA by ranking both clinical outcome and cost of care in the one or more bundles of predetermined patient care services.

In some embodiments, the visual classification of the list of medical professionals by clinical outcome comprises: (a) green signifying a better than average clinical outcome; (b) yellow signifying an average clinical outcome; and (c) red signifying a poorer than average clinical outcome.

In some embodiments, the non-transitory computer readable medium further comprises, with permission from the patient and the selected medical professional: transmitting the personal health information of the patient from the first clinical outcome tracking and analysis module, to a computing device comprising a fourth clinical outcome tracking and analysis module at the selected medical professional's office.

In some embodiments, the behavioral variance data for each medical provider at each CNA in (c) includes both necessary care that is absent and unnecessary care contributing to the medical care provider's adverse variance for patients at each CNA at the key points in time during treatment.

In some embodiments, the nontransitory computer readable medium further comprises indicating that the service is for the purpose of diagnosing or treating a medical condition.

In some embodiments, the cost report contains: a comparison between physician and average cost per revenue; or hospital contribution margin in dollars and percent comparisons; or hospital average revenue per patient; or hospital average cost per patient; or average cost per case for each physician, weight peer average; or average cost of imaging, lab work, evaluation and management; or pharmaceuticals, medical supplies and other expenses for each physician; or a combination thereof.

In some embodiments, the variables selected by the payer include variables that identify certain attributes of the personal health information as a desired set of characteristics; one or more attributes added by the payer to the personal health information to identify the personal health information of each patient as being on an equal level of importance to other health information in the patient population database, or both.

These and other aspects and embodiments will be apparent to those of ordinary skill in the art by reference to the following detailed description and the accompanying drawings.

BRIEF DESCRIPTION OF THE DRAWINGS

In the drawing figures, which are not to scale, and where like reference numerals indicate like elements throughout the several views:

FIGS. 15A and 15B are graphical representations of a treatment interface in accordance with an embodiment of the present disclosure;

FIG. 16. is a graphical representation of an outcome screen in accordance with an embodiment of the present disclosure;

FIGS. 21-23 display embodiments of graphical representations for different diagnosis types in accordance with an embodiment of the present disclosure;

DESCRIPTION OF EMBODIMENTS

Figure 1:
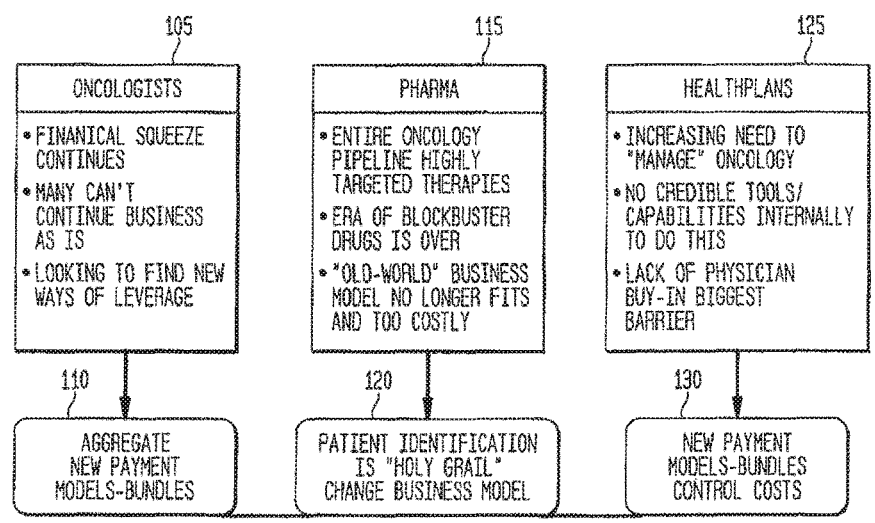
FIG. 1 illustrates a block diagram of an example of some of the pressures in the oncology market and some potential solutions.

Embodiments are now discussed in more detail referring to the drawings that accompany the present application. In the accompanying drawings, like and/or corresponding elements are referred to by like reference numbers.

Various embodiments are disclosed herein; however, it is to be understood that the disclosed embodiments and user interfaces as shown are merely illustrative of the disclosure that can be embodied in various forms. In addition, each of the examples given in connection with the various embodiments is intended to be illustrative, and not restrictive. Further, the figures are not necessarily to scale, some features may be exaggerated to show details of particular components (and any size, material and similar details shown in the figures are intended to be illustrative and not restrictive). Therefore, specific structural and functional details disclosed herein are not to be interpreted as limiting, but merely as a representative basis for teaching one skilled in the art to variously employ the disclosed embodiments.

The present invention is described below with reference to block diagrams and operational illustrations of methods and devices to select and present media related to a specific topic. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer, special purpose computer, ASIC, or other programmable data processing apparatus, such that the instructions, which execute via the processor of the computer or other programmable data processing apparatus, implements the functions/acts specified in the block diagrams or operational block or blocks.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved. Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Although described with respect to cancer conditions, the described clinical outcome therapeutic analysis can be used for any clinical condition (e.g., cardiovascular disease, metabolic disease (diabetes), immune mediated diseases (e.g., lupus, rheumatoid arthritis), organ transplantation; neurodegenerative disorders; pulmonary diseases, infectious diseases, hepatic disorders; behavioral health). A practitioner would know the parameters of each such condition.

Throughout the specification and claims, terms may have nuanced meanings suggested or implied in context beyond an explicitly stated meaning Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The pharmaceutical industry has placed most of its research and development (R&D) investments into specialty compounds with oncology as the lead category. For example, approximately 30-35% of Phase 3 pipeline is oncology. These compounds are highly targeted, specialized therapies based on latest scientific advances and will likely require a commercial and development model different from the one that exists today. Pharmaceutical companies' current structures are typically inefficient and likely cannot be supported by their future products.

Diagnostic companies developing new companion diagnostic tests for new generation therapies will need new ways to educate physicians and efficient sales and distribution channels.

The reimbursement model in the U.S. will likely change from a fee-for-service model to a value-based payment model. The Affordable Care Act has accelerated certain elements of this (e.g., accountable care organizations (ACOs) & patient centered medical home (PCMHs) models for primary care) and there is payer activity towards bundling payments within specialties (e.g. orthopedics). The current fee-for-service payment model is likely not sustainable for the government, employers, other payers, and/or for physicians. Many physicians are also finding the economics of a fee-for-service model unsustainable. As indicated above, the government is likely moving towards value-based payment models.

FIG. 1 illustrates a block diagram of an example of some of the pressures in, for example, the oncology market and some potential solutions. Oncologists 105 face financial pressures, many cannot continue business with their current models, and many are looking to find new ways of leverage. Potential oncologist solutions 110 include aggregating and new payment models, such as bundles. Pharmaceutical companies (shown as "Pharma") 115 typically have much or all of their oncology pipeline as highly targeted therapies. Additionally, the era of blockbuster drugs is likely over. Further, the "old-world" business model may no longer fit and may be too costly. Possible pharmaceutical solutions 120 include patient identification and changing their business model. Health plans 125 typically have an increasing need to "manage" oncology. Also, there are no credible tools or capabilities internally to perform this management. Additionally, medical professionals such as physicians may not buy into the health plans. Potential health plan solutions 130 include new payment models (e.g., bundles) and controlling costs.

Figure 2:
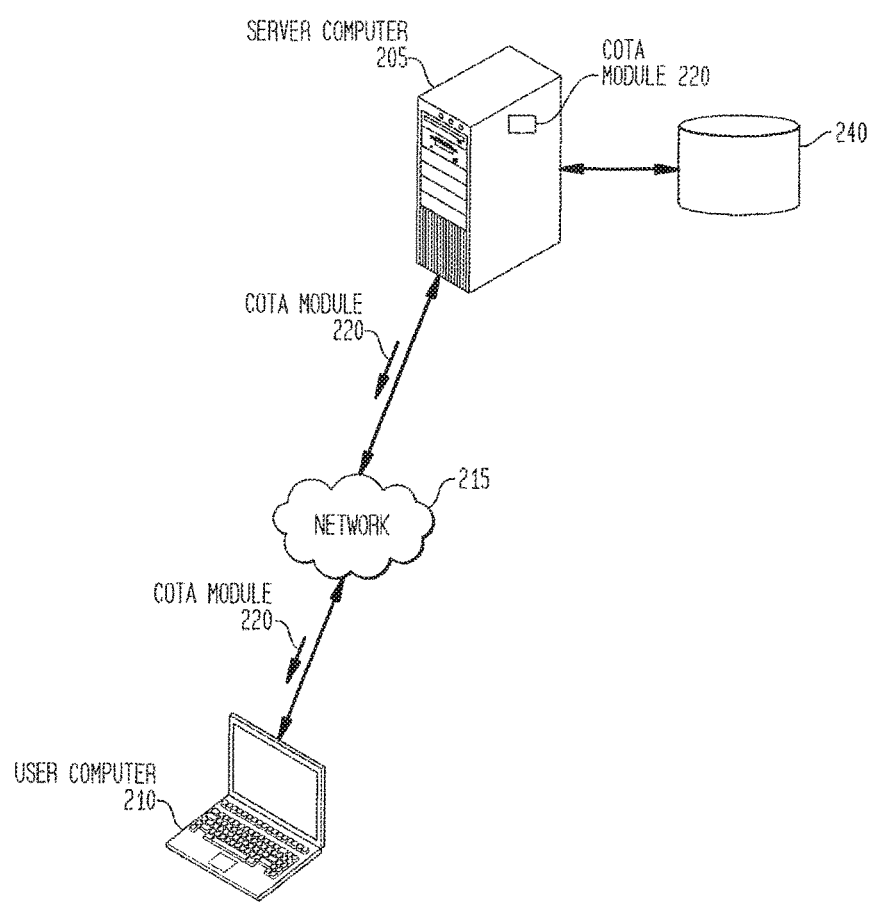
FIG. 2 illustrates a block diagram of a server computer communicating with one or more user computers over a network to provide a clinical outcome tracking and analysis (COTA) module to the one or more user computers in accordance with an embodiment of the present disclosure.

FIG. 2 illustrates a block diagram of a server computer 205 (also referred to below as server 205) communicating with a user computer (also referred to herein as client device) 210 and a user computer (also referred to herein as computing device) 230 over network 215 to provide a clinical outcome tracking and analysis (COTA) module 220 to the user computer 210 and/or user computer 230 in accordance with one embodiment. Server 205 may generate and/or serve web pages, for example, to be displayed by a browser (not shown) of user computer 210 and/or user computer 230 over network 215 such as the Internet. In one embodiment, the COTA module 220 is a web page (or is part of a web page) and is therefore accessed by a user of the user computer 210 and/or user computer 230 via a web browser. In another embodiment, the COTA module 220 is a software application, such as a mobile "app", that can be downloaded to the user computer 210 and/or user computer 230 from the server computer 205. In a further embodiment the COTA module 220 provides a user interface for enabling the functionality described herein.

A computing device such as server computer 205, user computer 210, and user computer 230 may be capable of sending or receiving signals, such as via a wired or wireless network, or may be capable of processing or storing signals, such as in memory as physical memory states. Devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows® Server, Mac® OS X®, Unix®, Linux®, FreeBSD®, or the like.

Server 205 may include a device that includes a configuration to provide content via a network to another device. Server 205 may, for example, host a site, such as a social networking site, examples of which may include, without limitation, Flickr®, Twitter®, Facebook®, LinkedIn®, or a personal user site (such as a blog, vlog, etc.). Server 205 may also host a variety of other sites, including, but not limited to, business sites, educational sites, dictionary sites, encyclopedia sites, wikis, financial sites, government sites, etc.

Server 205 may further provide a variety of services that include, but are not limited to, web services, third-party services, audio services, video services, email services, instant messaging (IM) services, SMS services, MMS services, FTP services, voice over IP (VOIP) services, calendaring services, photo services, or the like. Examples of content may include text, images, audio, video, or the like, which may be processed in the form of physical signals, such as electrical signals, for example, or may be stored in memory, as physical states, for example. Examples of devices that may operate as a server include desktop computers, multiprocessor systems, microprocessor-type or programmable consumer electronics, etc.

In one embodiment, the server 205 hosts or is in communication with a database 240. The database 240 may be stored locally or remotely from the server 205. In one embodiment, the COTA module 220 accesses or searches or sorts the data stored in database 240. The COTA module 220 may also retrieve information over network 215 (e.g., from the Internet). Database 240 may store patient data or other pertinent medical information. For example, the data entered into the database or the COTA module 220 may be from experts in their respective fields (e.g., oncologists with more than 5, 10, 15, 20, 30, etc. years of experience). The data can be entered into the database 240 and/or the COTA module 220 manually or automatically.

A network may couple devices so that communications may be exchanged, such as between a server and a client device or other types of devices, including between wireless devices coupled via a wireless network, for example. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, or any combination thereof. Likewise, sub-networks, such as may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a telephone line or link, for example.

A wireless network may couple client devices with a network. A wireless network may employ stand-alone ad-hoc networks, mesh networks, Wireless LAN (WLAN) networks, cellular networks, or the like. A wireless network may further include a system of terminals, gateways, routers, or the like coupled by wireless radio links, or the like, which may move freely, randomly or organize themselves arbitrarily, such that network topology may change, at times even rapidly. A wireless network may further employ a plurality of network access technologies, including Long Term Evolution (LTE), WLAN, Wireless Router (WR) mesh, or 2nd, 3rd, or 4th generation (2G, 3G, or 4G) cellular technology, or the like. Network access technologies may enable wide area coverage for devices, such as client devices with varying degrees of mobility, for example.

For example, a network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LIE Advanced, Wideband Code Division Multiple Access (WCDMA), Bluetooth, 802.11b/g/n, or the like. A wireless network may include virtually any type of wireless communication mechanism by which signals may be communicated between devices, such as a client device or a computing device, between or within a network, or the like.

In one embodiment and as described herein, the user computer 210 and/or user computer 230 are smartphones. In another embodiment, the user computer 210 and/or user computer 230 are tablets. The user computer 210 and/or user computer 230 can also be a computer, a music player, a set-top box, a smart TV, or any other computing device that can transmit information.

The COTA module 220 can establish an effective way to manage patients, resulting in better outcomes at controlled costs. In one embodiment, the COTA module 220 is the connector or interface between third parties and medical professionals (e.g., oncologists). In one embodiment, the COTA module 220 is an analytic tool that sorts cancers to the highest level of clinical and molecular fidelity. The COTA module 220 then tracks outcomes in real-time, such as overall survival (OS), Progression free survival (PFS), and cost.

Overall survival may be a trial endpoint, which is usually expressed as a period of time (survival duration), e.g., in months. Frequently, the median is used so that the trial endpoint can be calculated once 50% of subjects have reached the endpoint. An example is disease free survival, which is usually used to analyze the results of the treatment for the localized disease which renders the patient apparently disease free, such as surgery or surgery plus adjuvant therapy. In the disease-free survival, the event is relapse rather than death. The people who relapse are still surviving but they are no longer considered disease-free.

Progression free survival is the length of time during and after medication or treatment during which the disease being treated (e.g., cancer) does not get worse. It is sometimes used as a metric to study the health of a person with a disease to try to determine how well a new treatment is working.

As used herein, the term "real-time" or "real time" means without perceivable delay or information that is delivered immediately after collection or processing. These terms also include a time delay introduced by automated processing (e.g., near real-time).

In one embodiment, the COTA module 220 can alert the user of the user computer 210 and/or user computer 230 (e.g., medical professional) at key moments to provide relevant information. The COTA module 220 can also enable communication and collaboration between medical professionals as well as content publishing (e.g., by medical professionals). In one embodiment, COTA module 220 can enable medical professionals to execute at-risk contracts (e.g., bundled payments) with payers.

Although the COTA module 220 is described herein with respect to cancer, the COTA module 220 can be utilized advantageously to manage any disease or condition.

In one embodiment, descriptive elements of COTA include sorting, outcome tracking, performance status/quality of life metrics, toxicity to therapy and cost of care.

Figure 3:
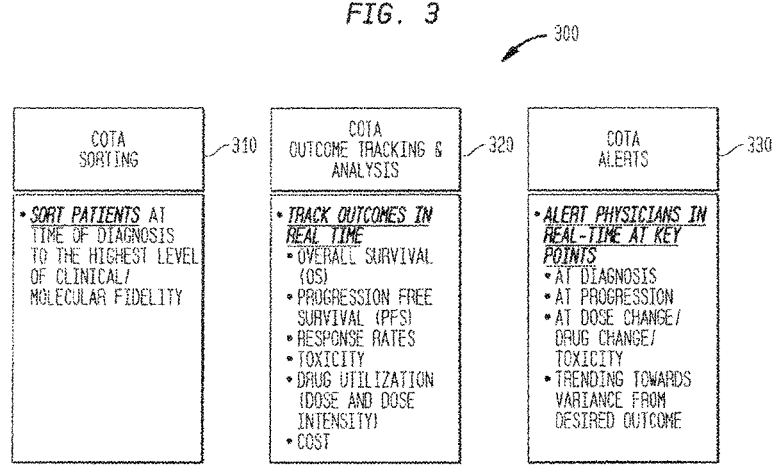
FIG. 3 is a block diagram illustrating several functions provided by the COTA module in accordance with an embodiment of the present disclosure.

FIG. 3 is a block diagram illustrating functions 300 provided by the COTA module 220 in accordance with one embodiment.

In one embodiment, the COTA module 220 performs COTA sorting 310, which identifies patients satisfying one or more parameters. Parameters may include, for example, demographic parameters, e.g., sex, age, ethnicity, comorbidities, tobacco use, medical record number, source of insurance, primary care medical professional, referring medical professional, hospital, approved service vendors (e.g., pharmacy), disease specific clinical and molecular phenotype, therapy intent, stage of therapy with respect to progression of disease, and biomarkers. The parameters may be a simple indicator (e.g., positive, negative, not accessed), a numerically based parameter (e.g., tumor size), a standards based parameter (e.g., tumor grade), etc. The parameters may be received by the COTA module 220 as a user selected input. Patients may be sorted 310 at the time of diagnosis to the highest level of clinical and/or molecular fidelity because each patient has different mortality, morbidity, treatments and costs. The term "highest level of clinical and/or molecular fidelity" refers to the highest level of patient information available according to the latest scientific and/or medical guidelines as accepted in its pertinent field. For example, where there are, e.g., 10 tests available for lung cancer, results of the 10 tests represent the highest level of fidelity for lung cancer. The COTA module 220 may sort patients with lung cancer with any combination of those 10 results. The COTA module 220 may include additional scientific and/or medical guidelines as they become accepted in its pertinent field. In one embodiment the COTA module 220 collects all information that impacts survival and/or prognosis and/or treatment of a patient based on the latest scientific and/or medical guidelines.

Further, the COTA module 220 performs outcome tracking and analysis 320. The COTA module 220 tracks outcomes in real time. In one embodiment, the element Outcome Tracking includes the parameters progression free survival, overall survival, performance status/quality of life metrics, incidence/severity of toxicity, (e.g., the degree to which a substance or drug can damage an individual), death, and drug utilization (e.g., delivered dose intensity, dose interval and duration of therapy) Other types of outcomes are also contemplated.

The element ECOG performance status/quality of life metrics refers to a method by which the quality of life of the patient over time can be tracked. It is part of the demographic parameter disease specific clinical molecular phenotype, i.e., the stage of a patient's health at the start of therapy, and is within Sorting. For example, a comparison of ECOG at start of therapy (e.g., ECOG of 3), with ECOG after therapy (e.g., ECOG of 2) reflects the effect of the therapy.

In one embodiment, exemplary parameters of the element Toxicity to Therapy are incidence and severity. In one embodiment, COTA enables at risk financial contracting between payers and providers so the parties can reduce variability, waste and inefficiency but yet deliver on the intended outcome.

The COTA module 220 can also transmit communications, such as alerts 330, to medical professionals (e.g., physicians) (or, in another embodiment, to a patient's insurance company or any other entity) in real-time at key points, such as, e.g., at diagnosis, at progression, at dose change/drug change/toxicity, and/or trending towards variance from desired outcome. In one embodiment, the COTA module 220 provides alerts to medical professionals that identify a specific patient for which the medical professional is searching. For example, the COTA module 220 may provide an alert in real time to a pharmaceutical company that is looking for specific patients to administer a specific (e.g., new) drug or drug candidate. The alert may identify a specific patient that is a good candidate for the specific drug.

Figure 4A:
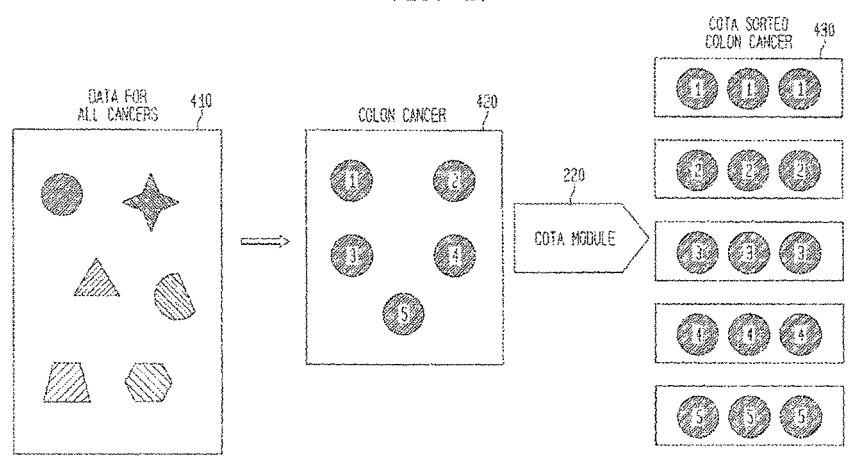
FIG. 4A is a block diagram illustrating use of the COTA module to sort data associated with colon cancer patients in accordance with an embodiment of the present disclosure.

FIG. 4A is a block diagram illustrating sorting data associated with colon cancer patients in accordance with one embodiment. Although described with respect to cancer, e.g., colon cancer, the description and figure can apply to any type of cancer or, in another embodiment, any type of disease for which there is data associated with patients.

Data 410 is gathered for all cancers (or, in another embodiment, for more than one type of cancer, or, in other embodiments, for all cardiovascular diseases, pulmonary diseases, gastrointestinal diseases, neurological diseases, etc), and this data 410 is narrowed to a subset 420 relating to, e.g., colon cancer. In one embodiment, the subset 420 of data relating to colon cancer is then analyzed and sorted by the COTA module 220 to produce a sorted colon cancer data set 430. The sorted colon cancer data set 430 can include one or more groupings, where each grouping includes data associated with patients having the same type of specific colon cancer. Thus, the COTA module 220 enables the sorting of cancers to the highest level of fidelity.

Typically, patient information is stored in electronic medical records (EMRs). EMRs, however, often contain too much information and it is therefore difficult for a medical professional to locate specific information of interest from the large amount of information stored in EMRs. Further, most of the information in EMRs is not relevant to the information for which the medical professional is searching. Unlike EMRs, whose goal is to capture all or most of the data associated with a patient coming into a doctor's office and the patient leaving the doctor's office, the COTA module 220 is targeted, as the module 220 enables a user to locate specific data associated with particular patients. Accordingly, the COTA module 220 can sort the data to locate specific, specialized information. The data that the COTA module 220 receives is typically via a web page, and is discrete (e.g., typically provided by a user selecting one or more choices in a drop down menu or via one or more check boxes).

The COTA module classifies, sorts, and facilitates the grouping of types of patients based on these variables results in the designation of a unique COTA nodal address (CNA), which embodies those classification variables. In one embodiment, data is ingested into the system via a human user or a technical process, e.g., an API, a layer (meaning a part of the application which performs a particular function) in the application looks at, and assesses, the information, e.g., whether it is correct, whether it is corrupt, what information is there, what information is missing//holes in the information, how it is formatted, spelling, etc., corrects any problems with the information it detects to date, and assigns a CNA to that set of information. In one embodiment, the CNA is an address to classify like data. In one embodiment, the COTA module identifies the relationship between different characteristics in a grouping, which allows COTA to classify information on any patient in the grouping. In one embodiment, the set of information sitting in the database is preassigned a CNA. In one embodiment, the COTA module takes a large amount of information that encompasses many different attributes, allows the user to identify certain of the attributes as a set of characteristics, and adds an attribute(s) to the information to say that the information is similar to other pieces of information in the database, i.e., this information is of the same kind/value as the other information. Accordingly, the nodal address is a number that enables a user to specifically compare like patients to like patients. This specificity allows for minimizing biological variability of outcome and as a consequence provides greater precision regarding the effect of therapeutic agents on outcome.

In one embodiment, a user wants to validate personal health information (PHI) from a patient, make sure it is correct in every way, and then assign the appropriate CNA. As used herein, personal health information (PHI) refers to any information in a medical record or designated record set that can be used to identify an individual patient and that was created, used, or disclosed in the course of providing a health care service such as diagnosis or treatment. Examples of personal identifiers in PHI include, without limitation, name, all geographical subdivisions smaller than a state, including street address, city, county, precinct, zip code; all elements of dates (except year) for dates directly related to an individual, including birth date, admission date, discharge date, date of death, and all ages over 89 and all elements of date (including year) indicative of such age; phone numbers; fax numbers; electronic mail addresses; social security numbers; medical record numbers; health plan beneficiary numbers; account numbers; certificate/license numbers; vehicle identifiers and serial numbers, including license plate numbers; device identifiers and serial numbers; web Universal Resource Locators (URLs); Internet Protocol (IP) address numbers; biometric identifiers, including finger and voice prints; full face photographic images and any comparable images; and any other unique identifying number, characteristic, or code (but not the unique code assigned by the investigator to code the data). This PHI is input for patient A into a browser. The PHI gets sent to a classification layer and a CNA is assigned, the CNA defining attributes of patient A's record. and then into the database, i.e., the set of patient attributes, which falls under this type of CNA, is joined to the CNA. Once this is complete, the next time a user logs into the application and accesses the database, the database will return all of patient A's information and the CNA assigned. Accordingly, the user immediately understands how this patient's symptoms/attributes should be handled, i.e., the user gets a snapshot of how that type of patient relates to other patients whose information is in the database.

Figure 4B:
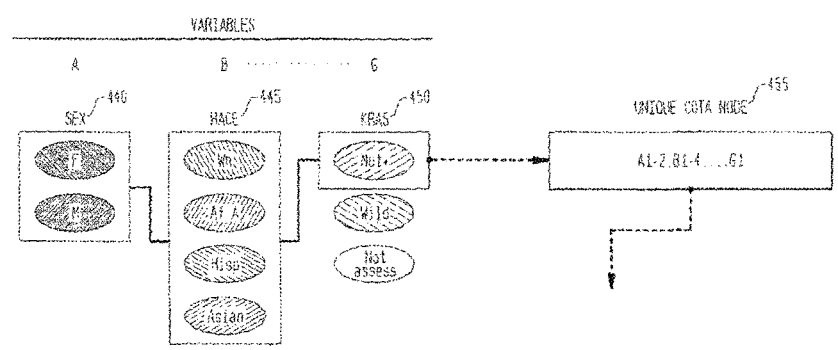
FIG. 4B is a flow diagram of the COTA module sorting data through specific node creation in accordance with an embodiment of the present disclosure.

FIG. 4B is a flow diagram of COTA classifying and sorting as described above through specific node creation in accordance with one embodiment As shown in FIG. 4B, an expert selects the variables sex or gender 440 (variable A), race 445 (variable B), . . . , and KRAS 450 (variable G). K-Ras is a protein that in humans is encoded by the KRAS gene. The protein product of the normal KRAS gene performs an essential function in normal tissue signaling, and the mutation of a KRAS gene is an important step in the development of many cancers.

The COTA module 220 analyzes the classified and sorted data 430 with respect to these variables (e.g., variables 440, 445, 450) to generate a unique COTA node 455. The COTA module 220 may apply these nodes on the classified and sorted data to provide more clinically relevant results. The nodes are created as a set of preselected variables which are applied to further filter the classified and sorted data. The nodes are represented as nodal addresses indicating the preselected variables. The variables may include, e.g., diagnoses, demographics, outcomes, phenotypes, etc. A phenotype is the composite of a person's observable characteristics or traits, such as its morphology, development, biochemical or physiological properties, phenology, behavior, and products of behavior. Phenotypes result from the expression of a person's genes as well as the influence of environmental factors and the interactions between the two. In one embodiment, the variables of a node are selected by experts in the pertinent field in order to partition the data into clinically relevant results.

The COTA node 455 is represented as a nodal address within the COTA module 220. In one embodiment, the nodal address is represented as a list of the variables selected (as a function of a letter representing the variable and a number representing the selection within the variable). For example, as shown in FIG. 4B, the node 455 includes A1-2 (A represents the sex or gender variable, and 1-2 represents Female and Male patients) shown with a block around both Female and Male variables of Sex variable A. The node 455 also includes B1-4 because the node 455 includes the Race variable with all of the sub-variables selected (shown with a box around all of the Race variables). The node 455 also includes G1, as with respect to the KRAS variable, only Mut+ is selected (boxed). Thus, node 455 has a node address of A1-2, B 1-4 . . . , G1.

In another embodiment, the node address is represented as a plurality of strings of digits separated by periods, where each string of digits indicates one or more variables (e.g., disease, phenotype, therapy type, progression/track, sex, etc.). For example, a first string of digits may represent a particular disease, a second string of digits may represent a type of the disease, a third string of digits may indicate a subtype of the disease, and a fourth string of digits may indicate a phenotype. Thus, in this example, the first string of digits may be 01 indicating cancer, the second string of digits may be 02 indicating breast oncology, a third string of digits may be 01 indicating breast cancer, and a fourth string of digits may be 1201 representing particular characteristics of a phenotype such that the nodal address is 01.02.01.1201. It should be understood that the nodal address may include any number of strings of digits and is not limited to four strings.

Figure 4C:
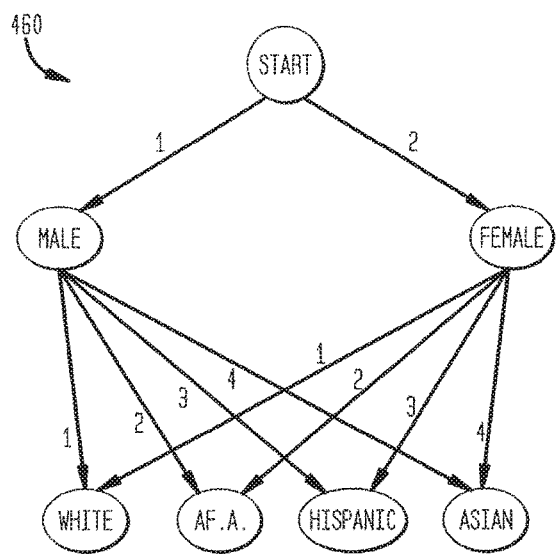
FIG. 4C is a block diagram illustrating a directed graph for determining a string of digits representing phenotype characteristics for nodal addressing in accordance with an embodiment of the present disclosure.

In one embodiment, the string of digits representing the phenotype may be provided by representing characteristics of the phenotype as a directed graph. FIG. 4C illustratively depicts a directed graph 460 showing characteristics of a phenotype to provide a string of digits representing the phenotype in accordance with one embodiment. The directed graph 460 includes nodes representing phenotypes and edges representing a relationship between nodes. The graph is traced starting from root "start" node to nodes for a selected phenotype. Each edge is associated with a number. The string of digits representing the phenotype for the node address is provided as a combination of the numbers. For example, the string of digits for selected phenotype characteristics of male and white would be represented as 11. Other types of combinations may also be employed. Advantageously, representing characteristics of the phenotype as a directed graph allows for the addition of other nodes without changing the entire structure. The screen's appearance is a result of the CNA, and its appearance can be changed however it is desired to present the information.

Node 455 provides the COTA module 220 with the ability to match resources and alerts specific to each phenotype where relevant. Resources can be information, content, link to live support, etc. Each patient is categorized into one or more nodal addresses. One or more nodes may also be associated with each disease. In one embodiment, resources get "tagged" with appropriate, relevant nodes. In one embodiment, nodes are fungible over time to stay current with scientific/medical advances.

Each nodal address may be associated with one or more bundles of predetermined patient care services (e.g., treatment plans). Each bundle may also be associated with one or more nodes. The services included in each bundle may be determined by one or more medical professionals, a hospital, a group, an insurance company, etc. to optimize patient care and/or cost. In one example, a bundle may indicate a number of imaging scans, a drug or choice of drugs, a schedule of when to administer the drugs, an operation or procedure, a number and frequency of follow up visits, etc. The bundling of patient care services may be particularly useful for risk contracting. For example, each bundle corresponding to a nodal address (associated with a particular disease) may have a predetermined cost allowing a user (e.g., doctor, patient, etc.) to choose an appropriate bundle. The cost may be determined or negotiated based on historical data associated with that particular disease or nodal address. Advantageously, the bundling of services provides cost certainty to an insurance company and/or hospital for a particular disease. This also reduces the cost of processing and maintaining records. Additionally, medical professionals will know ahead of time the predetermined course of treatment, which provides incentives to physicians to obtain better outcomes at lower costs.

The International Statistical Classification of Diseases and Related Health Problems 10th Revision (ICD-10) is a coding of diseases, signs and symptoms, abnormal findings, complaints, social circumstances and external causes of injury or diseases, as classified by the World Health Organization (WHO). These code sets, which are considered classification code sets, are at a higher level of information than some other medical code sets like the Systematized Nomenclature of Medicine (SNOMED), which is used by federal government systems for the electronic exchange of clinical health information. In one advantageous embodiment, nodal addresses are used to identify a course of treatment instead of using ICD-10 (International Classification of Diseases, 10th Revision) codes to identify and treat diseases. For example, this allows for a more effective course of treatment than the conventional ICD-10 codes for planning treatment, particularly where, for example, the patient is misdiagnosed.

Figure 5A:
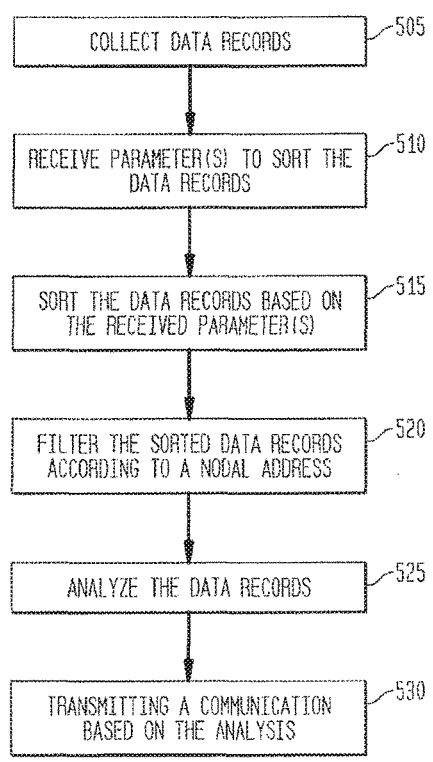
FIG. 5A is a flowchart illustrating steps performed by the COTA module in accordance with an embodiment of the present disclosure.

FIG. 5A is a flowchart illustrating steps performed by the COTA module 220 in accordance with one embodiment. At step 505, the COTA module 220 collects data records. The data records each include data associated with a disease (e.g., cancer). The data records may include patent data for patients who have or who previously had the disease. For example, the data records may include diagnoses, demographics, outcomes, costs, or other pertinent information. The data records may be collected from an electronic database (e.g., an electronic medical record), provided by a user (e.g., medical professional, expert, specialist, etc.), or from any other source. In one embodiment, the COTA module 220 stores the data records in database 240.

At step 510, the COTA module 220 receives one or more parameters to sort the data records. The one or more parameters may be received from the user computer 210 as user selected input. The one or more parameters may include, e.g., diagnoses, demographics, outcomes, costs, or any other parameter.

At step 515, the COTA module 220 sorts the data records based on the one or more parameters. The sorting identifies patients satisfying the one or more parameters. Patients are sorted to the highest level of clinical and/or molecular fidelity based on the latest scientific and/or medial guidelines accept in the pertinent field. In one embodiment, the sorting is performed in real time.

At step 520, the classified and sorted data records are filtered according to a nodal address. The nodal address represents variables preselected by users to provide a set of clinically relevant patients. In one embodiment, the variables of a nodal address are selected by experts in the field. The nodal address may be represented as a plurality of strings of digits each separated by a period. The each string of digits may represent one or more variables (e.g., a disease, type of disease, subtype of disease, phenotypes, or any other relevant variable). Other representations of the nodal address are also contemplated.

At step 525, the data records for the clinically relevant patients are analyzed. Analyzing the data records may include tracking (e.g., in real time) clinical outcomes of patients associated with the disease. The outcomes may include, for example, delivered dose intensity, therapeutic agents received, dose, dose interval, and dose duration, incidence and severity of toxicity, cost, progression free survival (PFS), overall survival (OS), response rates, etc. The COTA module 220 may compare the tracked outcomes between patients. The COTA module 220 may also determine, based on the tracking, whether a specific doctor associated with a tracked patient is treating the patient in accordance with treatment techniques of other doctors treating other (similar) patients. In one embodiment, the COTA module 220 determines this based on the outcomes of many patients.

In another embodiment, analyzing the data records may include updating (e.g., in real time) at least some of the data records based on the tracked outcomes. For example, the COTA module 220 may determine that patient ABC had colon cancer, was prescribed and has taken medication XYZ for two years, and is now in remission for the past 3 years. If the COTA module 220 determines this information from the tracking of patient ABC, the module 220 can update the data record associated with patient ABC with this information.

In other embodiments, analyzing the data records includes performing an analysis to determine patient survival rate, such as, e.g., by creating a Kaplan Meier curve. A Kaplan Meier curve is a curve that shows five year survival rate that can be developed, e.g., for a single doctor (or medical professional) or for a group of doctors (or medical professionals). A Kaplan Meier curve can be created for overall survival and/or progression free survival. Other types of analyses are also contemplated.

To facilitate analyzing, the COTA module 220 may also include an analysis tool to the user computer 210 and/or user computer 230. This analysis tool may be a user interface that is accessible via a web page, a tab on an existing web page, a software application, an app, etc. The user interfaces as depicted in the figures herein are exemplary. This analysis tool may enable a user to compare, analyze, or further sort the data records.

At step 530, the COTA module 220 provides a communication based on the analysis. The communication may be in the form of an alert to a user. In one embodiment, the COTA module 220 may communicate the classified and sorted data records and/or the updated data records to the user computer 210 and/or user computer 230. For example, the COTA module 220 communicates a table, chart, list, link, etc. that enables the user to access the sorted or updated data records. In another embodiment, the COTA module 220 may transmit advertisements with (e.g., related to) the data records to the user computer 210 and/or user computer 230. In other embodiments, the COTA module 220 may identify a specific patient as a candidate for a specific treatment or drug. This information may be valuable to, e.g., a pharmaceutical company, a health plan, a managed care consortium, an insurer, etc. The COTA module 220 may transmit the communication to the user computer 210, user computer 230, or any other entity (e.g., via network 215).

The COTA module 220 can be used by and benefit many people, professionals, and/or companies. For example and as described above, the highly specialized pipeline of pharmaceutical companies likely requires a new business model for many aspects (e.g., development including Phase 4 trials/post-marketing surveillance, marketing, sales, pricing, and contracting). In one embodiment, the professionals at the pharmaceutical companies can use the COTA module 220 to facilitate this new business model. For example, the COTA module 220 can match the right patient to the right drug. The COTA module 220 can enable precise patient identification via its sorting and nodal addressing abilities. In one embodiment, the COTA module 220 provides a matching function that enables a user (e.g., a pharmaceutical company) to locate (e.g., in real time) one or more patients that are or would be good candidates for a specific drug that the pharmaceutical company has released or is developing.

Further, the COTA module 220 may benefit health plans. As indicated above, cancer care will likely become more complex, and it will likely not be efficient for health plans to continue with direct management. In one embodiment, health plans outsource their cancer care to the COTA module 220 (similar to what health plans previously did with pharmacy benefits). This may reduce their costs, such as by reducing total cost of care and providing cost offsets for them, such as by replacing pathways, decreasing expensive prior authorization infrastructure, decreasing other personnel who "manage cancer". Additionally, provisions in the U.S. Affordable Care Act state that 85% of premiums must go to clinical care related activities versus administrative costs. In one embodiment, the COTA module 220 provides an analytic interface with connections to claims data to support health plans in managing their oncologists.

In one embodiment, the COTA module 220 can benefit organizations engaged in diagnostic methods or tools. Organizations engaged in diagnostic methods or tools, such as those involved in next generation genetic sequencing, will likely need an efficient education, marketing and sales/distribution channel. Because the COTA module 220 is able to precisely sort and identify patients and send time based alerts to physicians (or other medical professionals), its use may benefit such organizations.

Figure 5B:
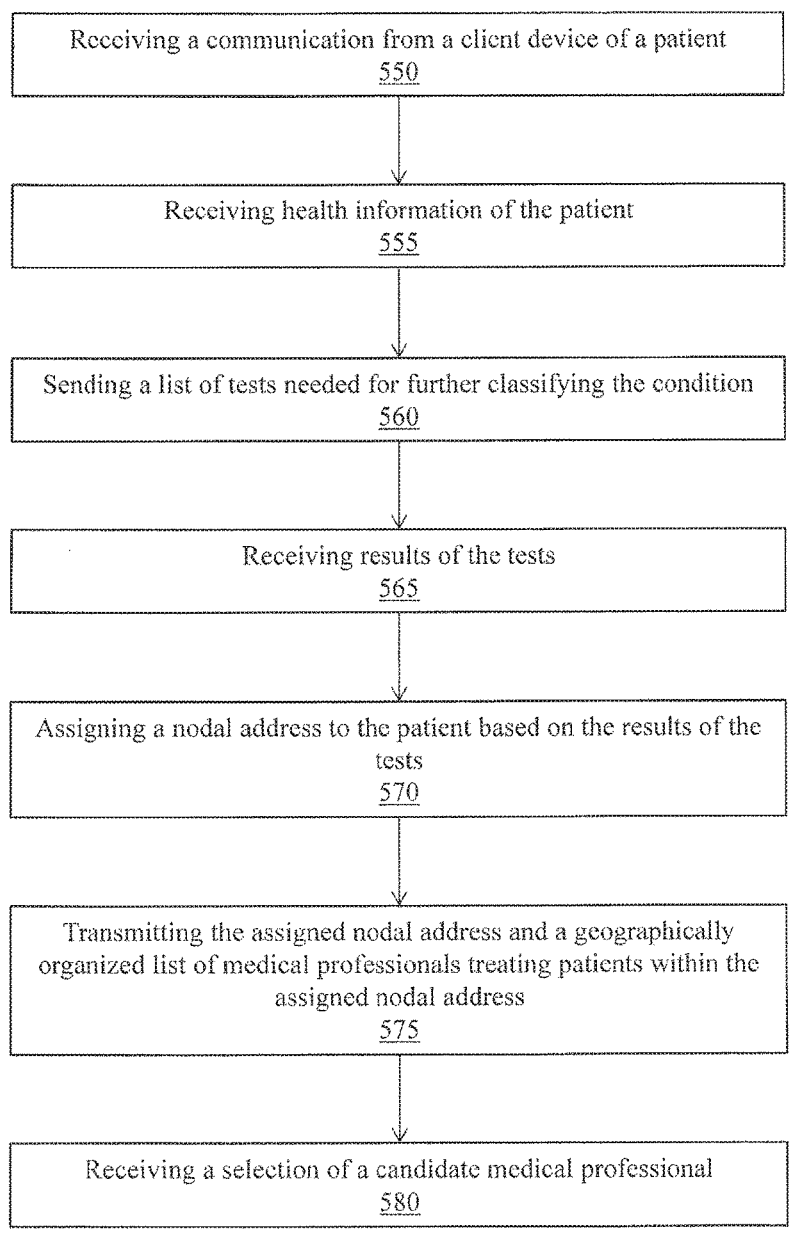
FIG. 5B is a flowchart illustrating steps for enabling a patient diagnosed with a condition to optimize treatment options in accordance with an embodiment of the present disclosure.

FIG. 5B is a flow chart illustrating steps for enabling a patient diagnosed with a condition to optimize his/her treatment options, in accordance with an embodiment. The steps of FIG. 5B may be performed by the COTA module 220 executing on server computer 205. The COTA module 220 executing on server computer 205 may interact with a user (e.g., a patient) via the COTA module 220 executing on user computer 210 and/or may interact with a user (e.g., a medical professional) via the COTA module 220 executing on user computer 230 over network 215. The COTA module 220 may include multiple instances of COTA module 220 for execution on server computer 205, user computer 210, and user computer 230.

At step 550, the COTA module 220 executing on server computer 205 receives a communication from user computer 210 of the patient. For example, the communication may include an indication that the patient is seeking treatment options, a medical professional, or any other indication. The COTA module 220 executing on server computer 205 is communicatively linked to database 240 comprising personal health information for a population of patients, which may or may not include health information of the patient. The COTA module 220 executing on server computer 205 is configured to analyze the personal health information stored in database 240. This may be performed as a pre-processing step, prior to receiving the communication from the patient. For example, the COTA module 220 executing on server computer 205 may analyze the personal health information as described herein by sorting and classifying the personal health information and assigning a plurality of nodal addresses to the each patient in the population of patients, measuring clinical outcomes for each nodal address, and measuring behavioral variance for each medical care provider assigned to each nodal address.

At step 555, health information of the patient is received. The health information may be received from the COTA module 220 executing on user computer 210. The health information of the patient may include the condition with which that the patient is diagnosed. In one embodiment, the condition is selected with specificity by the patient via the COTA module 220 executing on user computer 210 from lists and sublists of conditions available in the database 240 of computer server 205. The COTA module 220 executing on server computer 205 determines a list of tests for further classifying the condition based on the received health information of the patient.

At step 560, the list of tests needed by the COTA module 220 executing on server computer 205 for further classifying the condition is sent to the COTA module 220 executing on user computer 210.

At step 565, results of the tests are received from the COTA module 220 executing on user computer 210. The results of the tests may be sent from the patient after completing initial treatment and with permission from the patient to a medical professional to provide the results of the tests to the COTA module 220 executing on server computer 205.

At step 570, a nodal address is assigned to the patient based on the results of the tests. The assigned nodal address may be assigned from the plurality of nodal addresses generated during the pre-processing step by the COTA module 220 executing on server computer 205 for the population of patients. The assigned nodal address includes the set of preselected variables effective to partition the sorted and classified personal health information into a clinically relevant set of health information. In one embodiment, the assigned nodal address is associated with one or more bundles of predetermined patient care services (e.g., treatment plans) for treatment of the condition. The predetermined patient care services may be determined by one or more of a medical professional, a hospital, a medical group, or an insurance company. The bundles of predetermined patient care services may provide a predetermined course of treatment. The bundles of predetermined patient care services may provide cost certainty for the condition.

At step 575, the COTA module 220 executing on server computer 205 transmits the assigned nodal address and a geographically organized list of medical professionals treating patients within the assigned nodal address to the COTA module 220 executing on user computer 210. The geographically organized list of medical professionals may be visually classified by clinical outcome. In one embodiment, the geographically organized list of medical professionals may be visually classified by clinical outcome according to color. For example, the geographically organized list of medical professionals may be visually classified such that green signifies a better than average clinical outcome, yellow signifies average clinical outcome, and red indicates poorer than average clinical outcome.

At step 580, a selection of a candidate medical professional is received. The selected candidate medical professional may be selected by the patient to meet one or more of geographical limitations, clinical outcome criteria, and cost criteria set by the patient. In one embodiment, at the option of the patient, after receiving the selection of the candidate medical professional, each medical professional is further classified within the group of candidate medical professionals based on cost of care. For example, each medical professional may be further classified as being more, less, or substantially the same as the selected candidate medical professional.

In one embodiment, user computer 210 of the patient is communicatively linked to user computer 230 of a medical professional (e.g., at the office of the selected candidate medical professional) to facilitate scheduling of an appointment with the selected candidate medical professional. In another embodiment, the COTA module 220 executing on server computer 205 transmits the personal health information of the patient to the COTA module 220 executing on user computer 230 of the medical professional.

Advantageously, the steps of FIG. 5B enable a patient diagnosed with a condition to optimize treatment options based on geographical limitations, clinical outcome, and cost criteria of the patient.

Figure 6:
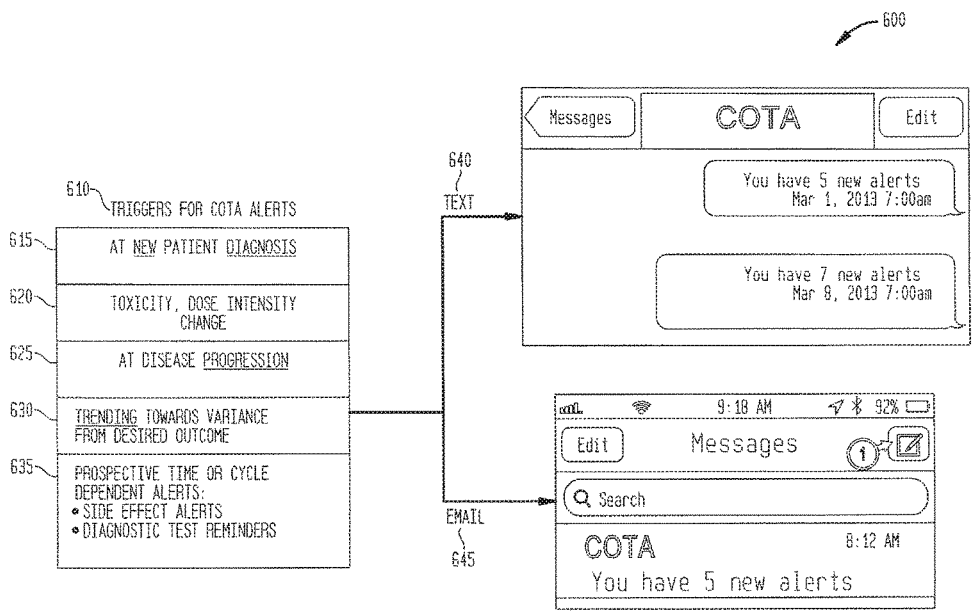
FIG. 6 illustrates a flow diagram of the COTA module transmitting alerts in response to triggers in accordance with an embodiment of the present disclosure.

FIG. 6 illustrates a flow diagram 600 of alerts provided by the COTA module 220 in accordance with an embodiment. In one embodiment, physicians or other medical professionals are alerted based on their preferences. These preferences can be set by the medical professional/physician and can include, for example, triggers 610 for the alerts and/or the technique used to provide the alert. A trigger for an alert can include, for example, at new patient diagnosis 615, an update to a diagnosis, real-time scheduled event, changes to group membership (e.g., a new gene identified which might change grouping, and/or someone leaving the group), toxicity and/or dose intensity change 620, at disease progression 625, administration of a particular drug, trending towards variance from desired outcome 630, and/or prospective time or cycle dependent alerts 635 (e.g., side effect alerts and/or diagnostic test reminders). The alert may include a text message 640 or an email 645 sent to the user computer 210. Other types of alerts are also contemplated, such as, e.g., a telephone call to the user computer 210, an update on a web page, a social media update, a message sent using, e.g., Twitter®, Facebook®, or other social media site, adding content to a software library or web page, and/or any other message or communication sent to or accessed by the user computer 210. Although described above as providing alerts, a trigger can be any action that results in the COTA module 220 performing any other action.

Figure 7:
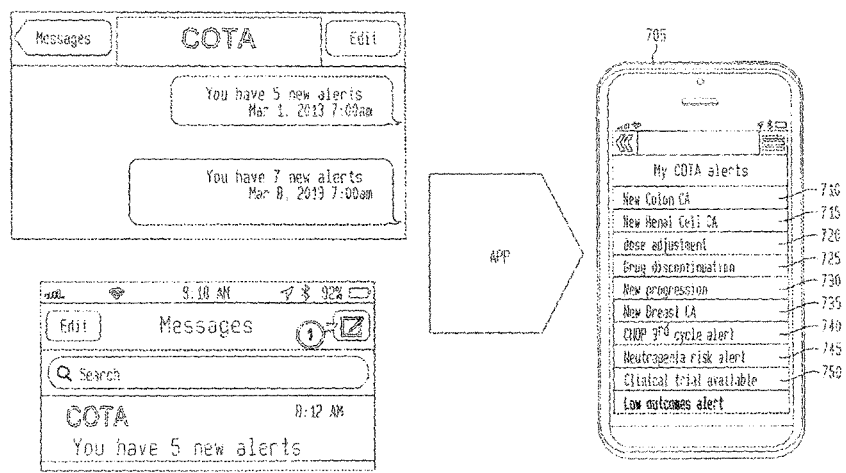
FIG. 7 is a graphical representation illustrating a mobile device organizing received alerts in accordance with an embodiment of the present disclosure.

FIG. 7 is a graphical representation illustrating a mobile device 705 (e.g., user computer 210) organizing alerts received by the device 705 in accordance with one embodiment. As shown in FIG. 7, the COTA alerts received are listed by a title or subject, such as New Colon CA 710, New Renal Cell CA 715, Dose Adjustment 720, Drug Discontinuation 725, New Progression 730, New Breast CA 735, CHOP 3$^{rd}$ cycle alert 740, Neutropenia risk alert 745, and Clinical trial available 750. CHOP is an abbreviated name of a combination of drugs used in chemotherapy, which includes cyclophosphamide (Cytoxan/Neosar), doxorubicin (or Adriamycin), vincristine (Oncovin), and prednisolone, and is used, for example, to treat non-Hodgkin lymphoma.

The COTA module 220 can provide specific disease data sets (e.g., on demand and in real time) including, for instance, incidence of disease (e.g., by a COTA sort), progression free survival by progression status, and/or overall survival. In one embodiment, the COTA module 220 can provide a drug utilization data set, such as data associated with a full or partial therapy, toxicity, and/or a change in therapy.

Figure 8:
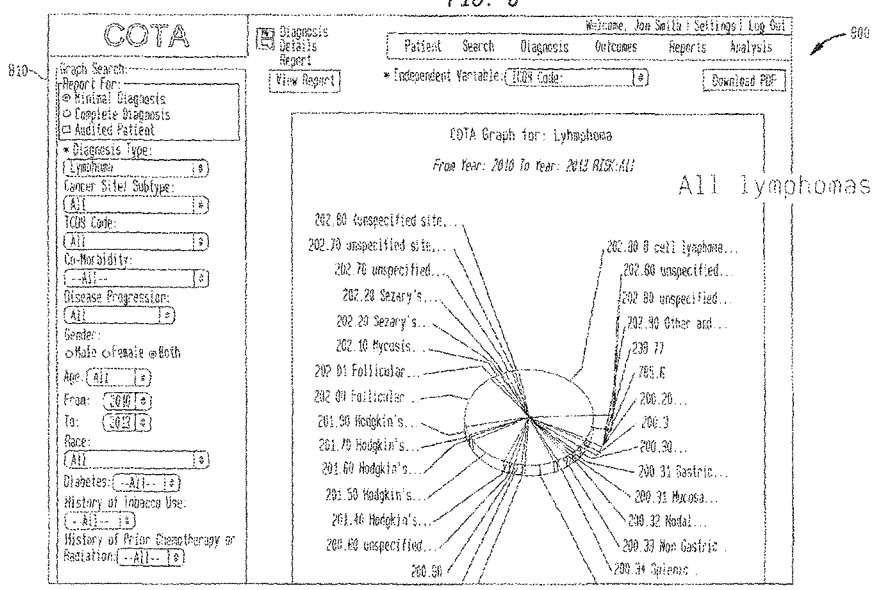
FIG. 8 shows a graphical representation of incidence of disease by cancer subtype in accordance with an embodiment of the present disclosure.

FIG. 8 shows a graphical representation 800 of incidence of disease by cancer subtype that can be provided by the COTA module 220 in accordance with one embodiment. Here, the COTA graph 800 is for lymphoma from years 2010 to 2013. A user can utilize a graph search input section 810 to narrow the information that is graphed. The graph search input section 810 can include, for example, a selection of what to report for (e.g., minimal diagnosis, complete diagnosis, and/or audited patient, diagnosis type, cancer site/subtype, ICD9 (International Classification of Diseases, Ninth Revision) code, Co-Morbidity, Disease Progression, Gender, Age, Date Range, Race, Diabetes, History of Tobacco Use, History of Prior Chemotherapy or Radiation, etc.

Figure 9:
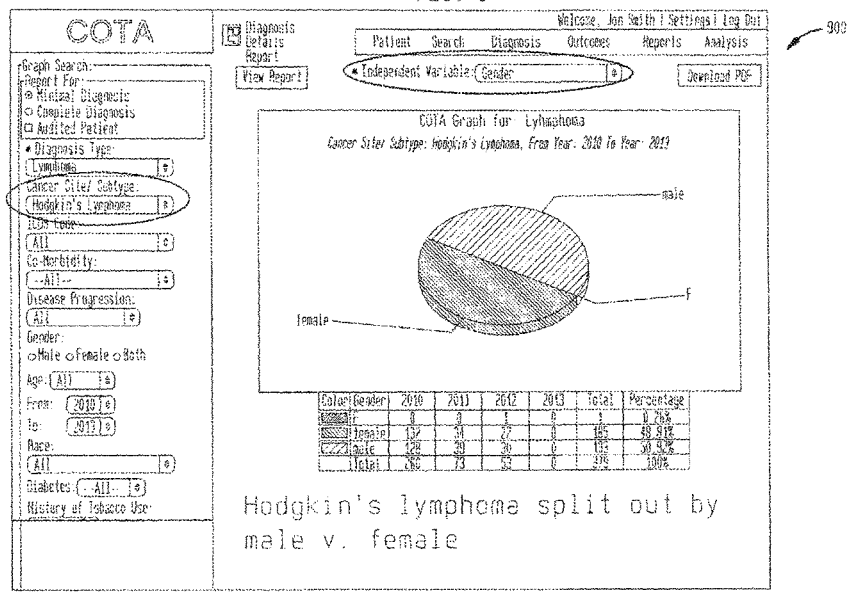
FIG. 9 is a graphical representation of a search refined by variables input into the COTA module in accordance with an embodiment of the present disclosure.
Figure 10:
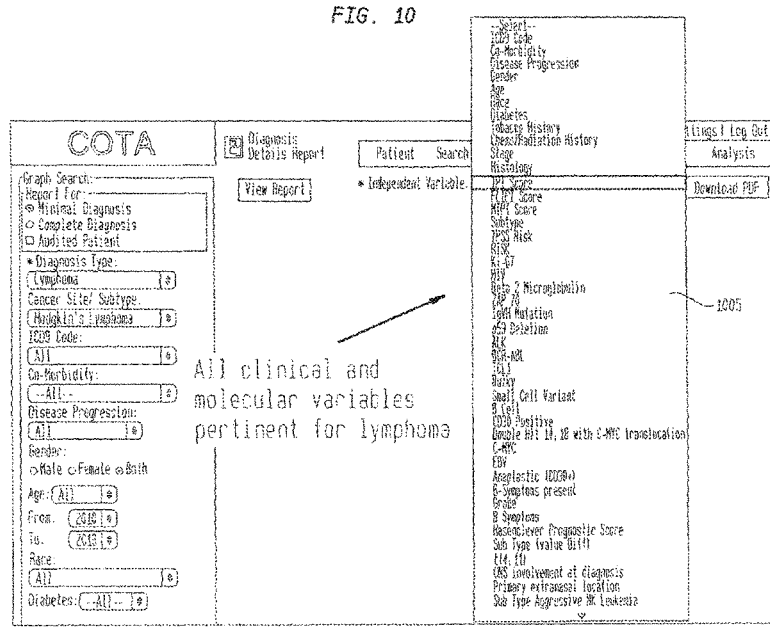
FIG. 10 shows a listing of a plurality of variables pertinent to a particular disease in accordance with an embodiment of the present disclosure.

FIG. 9 shows a graphical representation 900 of a sort based on variables input into the COTA module 220 that can be provided by the COTA module 220 in accordance with one embodiment. The graphical representation 900 shows a COTA graph for Hodgkin's Lymphoma from years 2010-2013 split out by male vs. female. The graphical representation 900 shows statistics 910 of the different patients who had this disease that were graphed in representation 900. FIG. 10 shows an exemplary listing of a plurality of variables 1005 pertinent to a particular disease (here, variables shown are for lymphoma) in accordance with one embodiment.

Figure 11:
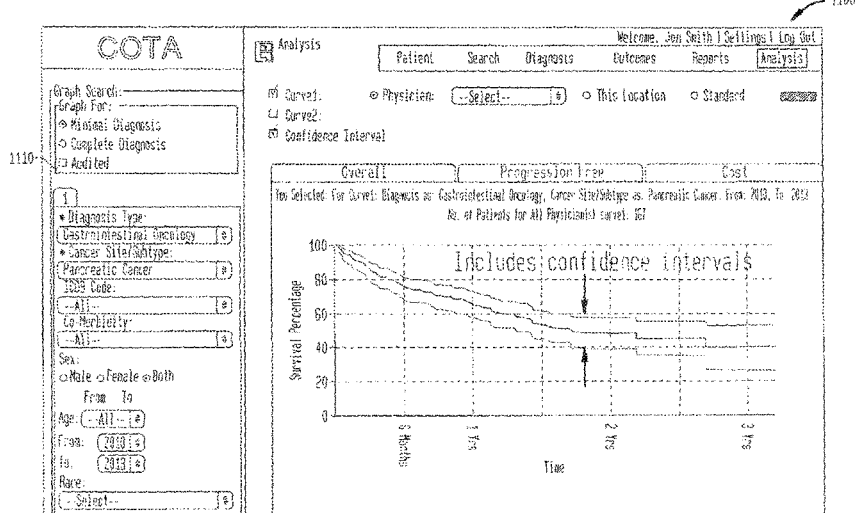
FIG. 11 shows a graphical representation including real-time Kaplan Meier curves with confidence intervals for pancreatic cancers in accordance with an embodiment of the present disclosure.

FIG. 11 shows a graphical representation 1100 including real-time Kaplan Meier curves with confidence intervals for pancreatic cancers that can be provided by the COTA module 220 in accordance with one embodiment. As described above, a Kaplan Meier curve is a curve that shows five year survival rate that can be developed, e.g., for a single doctor (or medical professional) or for a group of doctors (or medical professionals). A Kaplan Meier curve can be created for overall survival and/or progression free survival. The user indicates variables for his graph search in graph search input section 1110.

Figure 12:
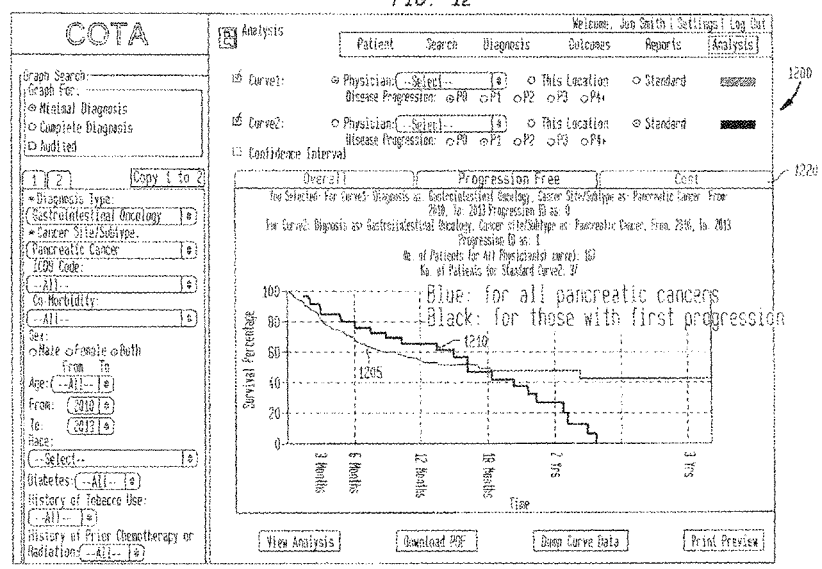
FIG. 12 is a graphical representation showing Kaplan Meier curves by disease progression in accordance with an embodiment of the present disclosure.

FIG. 12 is a graphical representation 1200 showing Kaplan Meier curves for disease progression that can be provided by the COTA module 220 in accordance with one embodiment. Line 1205 is for all pancreatic cancers, and bold line 1210 is for those with first progression.

Figure 13:
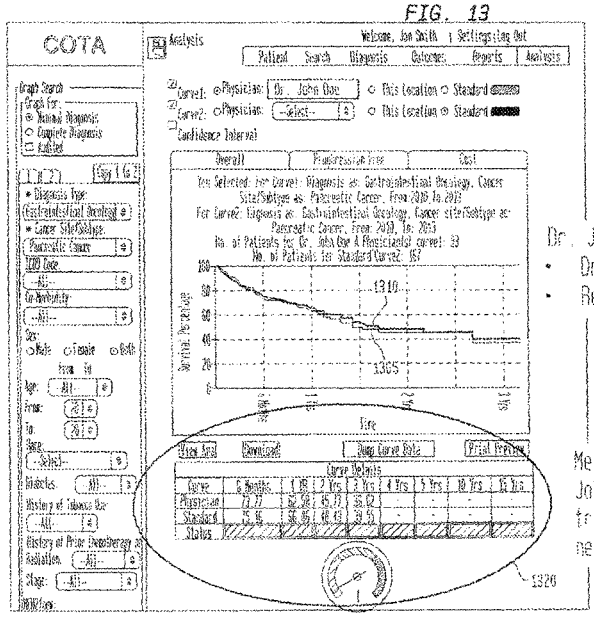
FIG. 13 is a graphical representation of real-time benchmarking of outcomes between two parties in accordance with an embodiment of the present disclosure.

FIG. 13 is a graphical representation 1300 of real time benchmarking of outcomes between two parties that can be provided by the COTA module 220 in accordance with one embodiment. The graph 1300 includes curve 1305 for outcomes of Dr. John Doe, a physician who treats pancreatic cancer, and a curve 1310 for outcomes of the rest of the doctors who treat pancreatic cancer. FIG. 13 also includes a meter 1320 measuring whether Dr. John Doe's outcomes are tracking positively or negatively.

Figure 14:
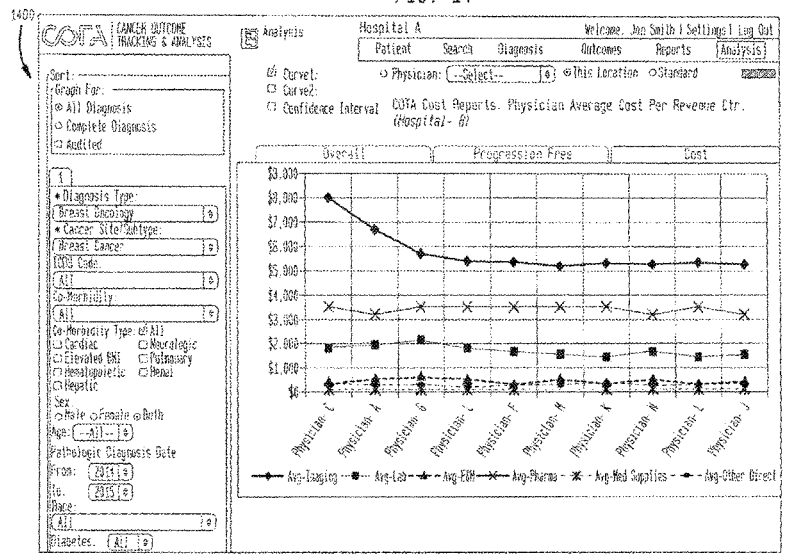
FIG. 14 is a graphical representation of a cost report in accordance with an embodiment of the present disclosure.

FIG. 14 is a graphical representation of a cost report 1400 associated with (e.g., provided by) the COTA module 220 in accordance with one embodiment. The screen's appearance is a result of the CNAs and its appearance can be changed however it is desired to present the information. The cost report 1400 may be associated with the cost tab 1220 of FIG. 12. The cost report 1400 can be used, for example, in estimating cost(s) of treatment, capturing knowledge, and/or transforming the knowledge into specific implementations. In one embodiment, the COTA module 220 tracks costs of various treatments, physicians, hospitals, etc. in real time. As shown in FIG. 14, the cost report 1400 illustrates a comparison between physician and average cost per revenue. Cost report 1400 may also include other comparisons, such as, e.g., hospital contribution margin in dollars and percent, hospital average revenue and cost (e.g., average revenue per patient, average cost per patient), physician average cost per case (e.g., average cost per case for each physician, weight peer average), physician average cost per revenue (e.g., average cost of imaging, lab work, evaluation and management, pharmaceuticals, medical supplies, and other expenses for each physician), etc.

Figure 15A:
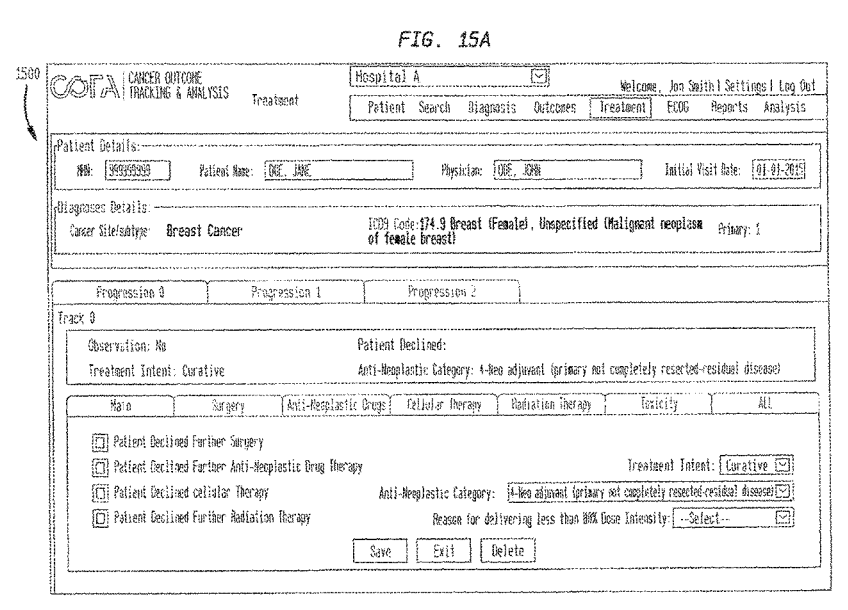
Figure 15B:
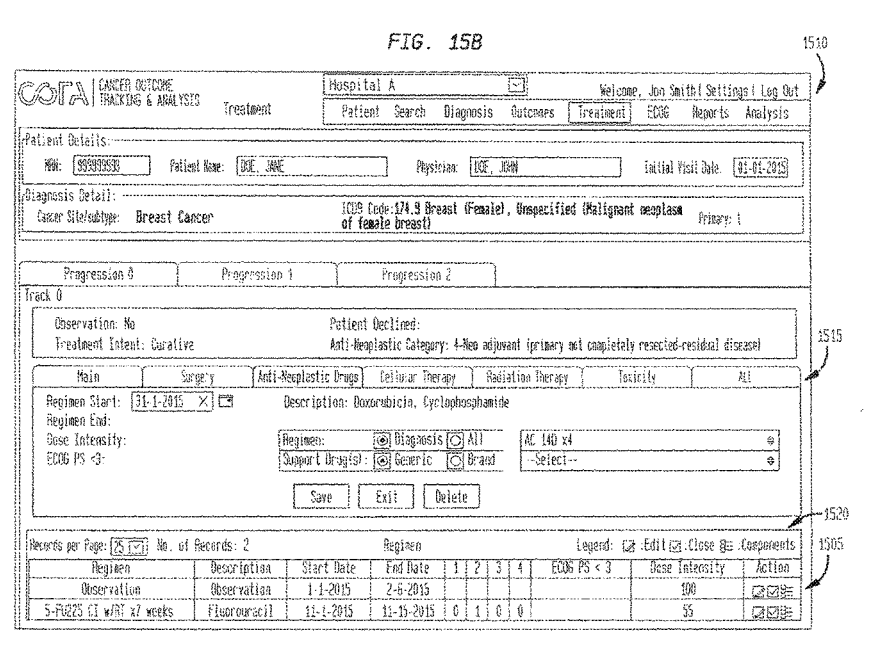

FIGS. 15A and 15B are graphical representations of a treatment interface 1500 associated with (e.g., provided by) the COTA module 220 for facilitating the connection between outcomes and treatments, in accordance with one embodiment. As shown in FIG. 15A, the treatment interface 1500 may include a list the different types of treatment administered to (or declined by) a patient with breast cancer, such as, e.g., surgery, antineoplastic drugs, cellular therapy, radiation therapy, etc. Treatment may be arranged according to a disease progression. For example, drugs in oncology are typically given in cycles, and, in any one cycle, any number of drugs can be given. In one embodiment, a user can select a progression (e.g., represented as progression 0 to progression 4), with progression 0 being after first diagnosis, cycle, and can select drugs in or from multiple categories.

In FIG. 15B, in another embodiment, a treatment interface 1510 may include treatment regimens for one or more therapies, graphically represented on treatment interface 1510 as tabs 1515. Treatment interface 1510 may include fields to indicate a start and end data for the regimen, dose intensity, description of treatment, specific brands of drugs, etc. Treatment regimens may be graphically summarized or represented as a listing of treatments in table 1520. Table 1520 may include action icons 1505 for each treatment. The action icons 1505 may facilitate actions, such as, e.g., editing, closing, viewing components, etc. In one embodiment, the action icons 1505 may be shortcuts to perform complex tasks (e.g., requiring multiple clicks or selections) with a single selection. For example, an icon on the diagnosis line can bring the user to the diagnosis screen.

Figure 16:
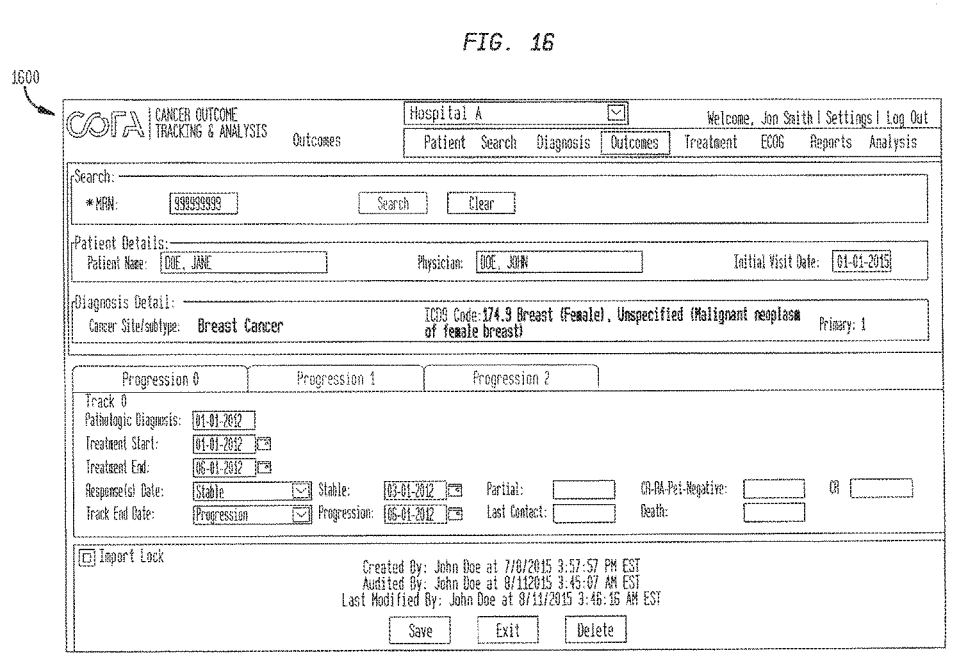

FIG. 16 is a graphical representation of an outcome screen 1600 for facilitating outcome tracking in accordance with one embodiment. Outcome screen 1600 may facilitate outcome tracking from, for example, diagnosis (i.e., progression zero), first progression, second progression through fourth progression, with each progression considered a different disease. The outcome screen tab can include (e.g., in one or more drop down menus or other fields) a diagnosis date, a treatment start and end date, a response to treatment (e.g., complete, partial, stable) and date of response, input fields for notes on the response (e.g., the partial field, CR-RA-Pet Negative field, the CR field, etc.), and a track end data, which may include fields for last contact and death. The outcome screen 1600 may also include other fields, such as, e.g., toxicity of a drug treatment, an input area enabling the input of what happened (e.g., discontinued, continued, no change, drug dosage change, and how many times), number of delays, number changes in drug, and/or number reduced. In one embodiment, a user of the COTA module 220 can flag a patient.

Figure 17:
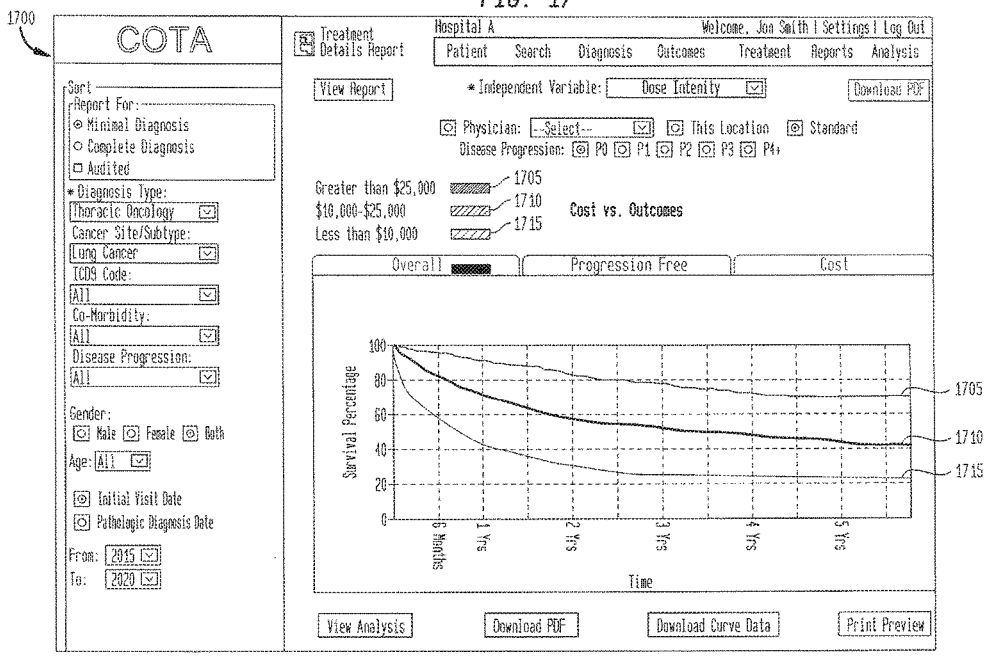
FIG. 17 is a graphical representation of a treatment details report screen in accordance with an embodiment of the present disclosure.

FIG. 17 is a graphical representation of a treatment details report screen 1700 illustrating a comparison between cost and outcome in accordance with one embodiment. The treatment details report screen 1700 correlates cost of care to clinical outcome to optimize value of care. Cost and financial data may be collected and analyzed by hospital, by doctor, etc. over a given time period (e.g., 5 years). The cost and financial data may be represented in one or more ranges of cost. In one embodiment, the ranges of cost include range 1705 for cost greater than $25,000, range 1710 for cost from $10,000 to $25,000, and range 1715 for cost less than $10,000. When combined with clinical data, the COTA module 220 may provide cost data for different treatments for a given time period based on different clinical sorts.

Figure 18:
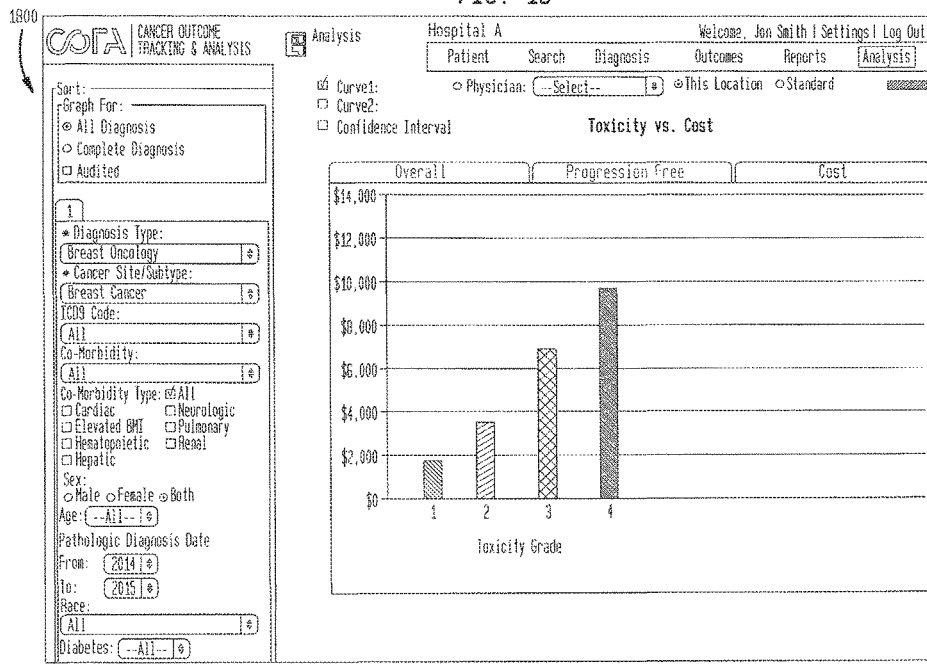
FIG. 18 is a graphical representation of an analysis screen comparing toxicity and cost in accordance with an embodiment of the present disclosure.

FIG. 18 is a graphical representation of an analysis screen 1800 provided by the COTA module 220 illustrating a comparison between toxicity and cost in accordance with one embodiment. The screen's appearance is a result of the CNAs and its appearance can be changed however it is desired to present the information. The analysis screen 1800 correlates incidence and severity of toxicity to cost of care and outcomes of care. The toxicity may be represented numerically (e.g., in ranges), by standards (e.g., grades), etc. For example, as shown in FIG. 18, toxicity is represented as toxicity grades 1-4 based on the Common Terminology Criteria for Adverse Events (CTCAE) classification. The grade of toxicity is graphically compared with cost. The analysis screen 1800 may be used to optimize value and efficacy of care, where value is efficacy/cost. In one embodiment, the COTA module 220 attempts to obtain high efficacy and low cost.

Figure 19:
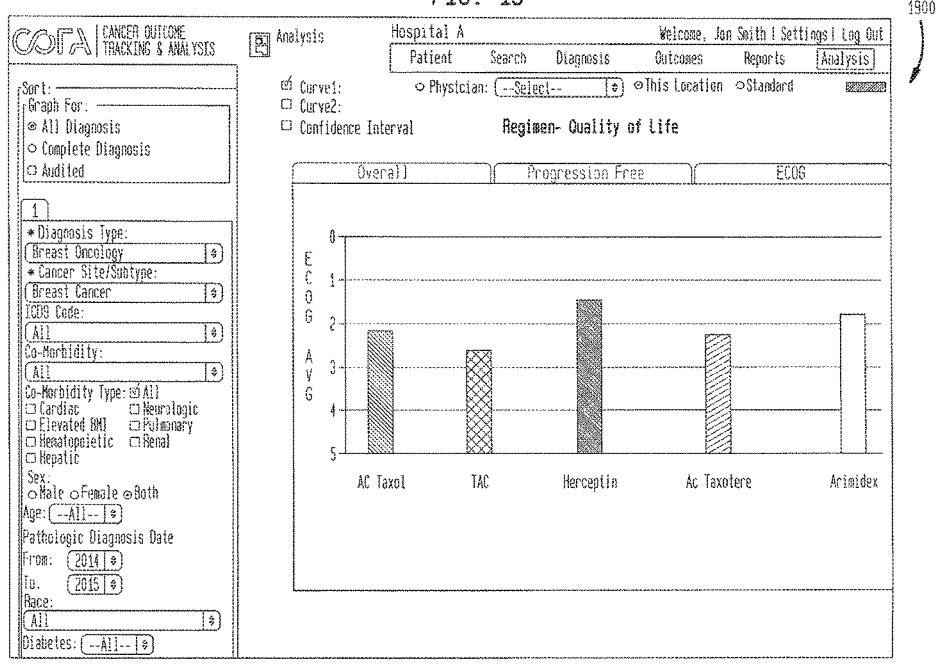
FIG. 19 is a graphical representation of an analysis screen comparing therapy and quality of life in accordance with an embodiment of the present disclosure.

FIG. 19 is a graphical representation of an analysis screen 1900 provided by the COTA module 220 illustrating a comparison between therapy and quality of life in accordance with one embodiment. The therapy may be represented by treatment drugs in analysis screen 1900. However, other forms of therapy are also contemplated, such as, e.g., surgery, procedures, etc. In one embodiment, the therapy includes an incidence, severity, and toxicity of therapy. Quality of life may be measured based on the average ECOG (Eastern Cooperative Oncology Group) scale, ranging from Grade 0 (i.e., fully active) to Grade 5 (i.e., dead). Quality of life may also be measured using any suitable metric. Analysis screen 1900 may facilitate assessment of how a patient's disease is progressing, how the disease affects the daily living abilities of the patient, and appropriate treatments and prognoses.

Figure 20:
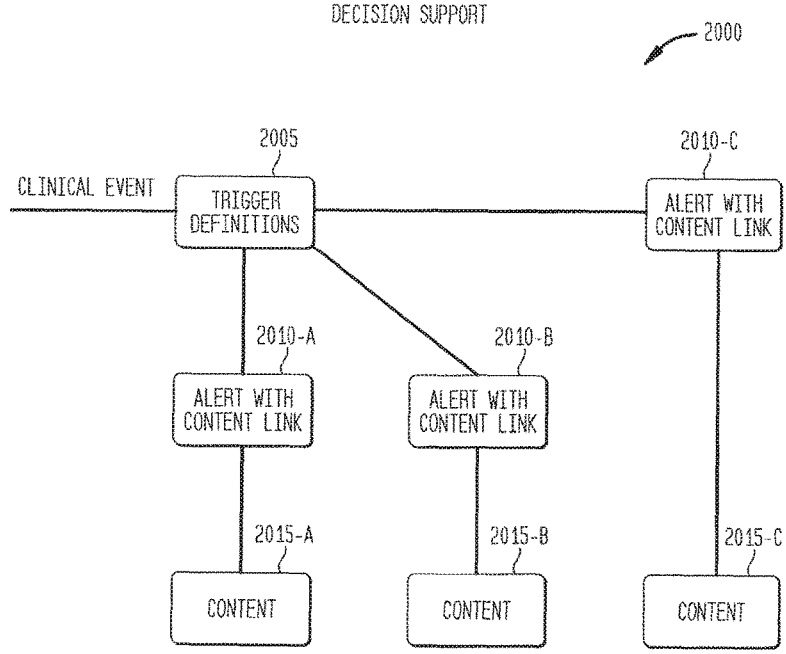
FIG. 20 is a flow diagram of feedback support provided to a medical professional in accordance with an embodiment of the present disclosure.

FIG. 20 is a flow diagram 2000 illustrating the alert system provided to a medical professional in accordance with one embodiment. The screen's appearance is a result of the CNAs and its appearance can be changed however it is desired to present the information. In one embodiment, the information in the alert is helping the user to make a decision in the future. In one embodiment, the information in the alert is providing a set of attributes that happened in the past time period. In one embodiment, it is both proactively influencing decisions of the user and reactively providing a digest report of how the medical personnel/Doctor did in the past week, month, quarter, etc. In one embodiment, there are different alerts for different users, each of which can influence decisions that the user makes. The alert may be employed for real time course correction to drive best value, such as, e.g., where an administered therapy deviates from a desired outcome. In block 2005, definitions are triggered based on clinical data. The definitions may be triggered using any criteria, such as, e.g., new disease diagnosis, disease progression, patient response, change in patient characteristics, dose change/drug toxicity change, trend towards variance from a desire outcome, etc. The criteria may be adjusted based on the disease and its parameters. Based on the triggered definitions, alerts 2010-A, 2010-B, 2010-C (collectively referred to as alerts 2010) are transmitted. It should be understood that alerts 2010 may include any number of alerts. The alerts 2010 may include content or a link to content. The alerts 2010 may be transmitted to the responsible physician, other medical professionals, hospital, pharmaceutical company, or any other person or entity.

Content 2015-A, 2015-B, 2015-C (collectively referred to as content 2015) is displayed, e.g., using user computer 210 to provide the alert. The content 2015 may include the patient data associated with the alert 2010, a comparison, or any other relevant content. In one embodiment, the comparison may be, e.g., between physicians, between one physician's patients and the whole patient population, between one physician and all physicians at a particular location, etc. The comparison may be based on a trending analysis to show where treatment is trending and if it is going off course (i.e., results are not as good as the standard). The comparison may be graphically displayed as one or more curves on a graph. In one embodiment, the COTA module 220 is utilized with cloud-based computing. The COTA module 220 can also enable or utilize connectivity to hospital records.

In one embodiment, the content 2015 may include feedback support to the medical professional having traffic light feedback indicators (not shown) on a display. For example, blue may mean very good performance (i.e., better than standard), green may mean standard performance, yellow may mean sufficient performance but may need to pay attention, red may mean the user may need to pay attention to something regarding the medical professional's approach to this disease. Other implementations of feedback indicators may also be employed.

Figure 21:
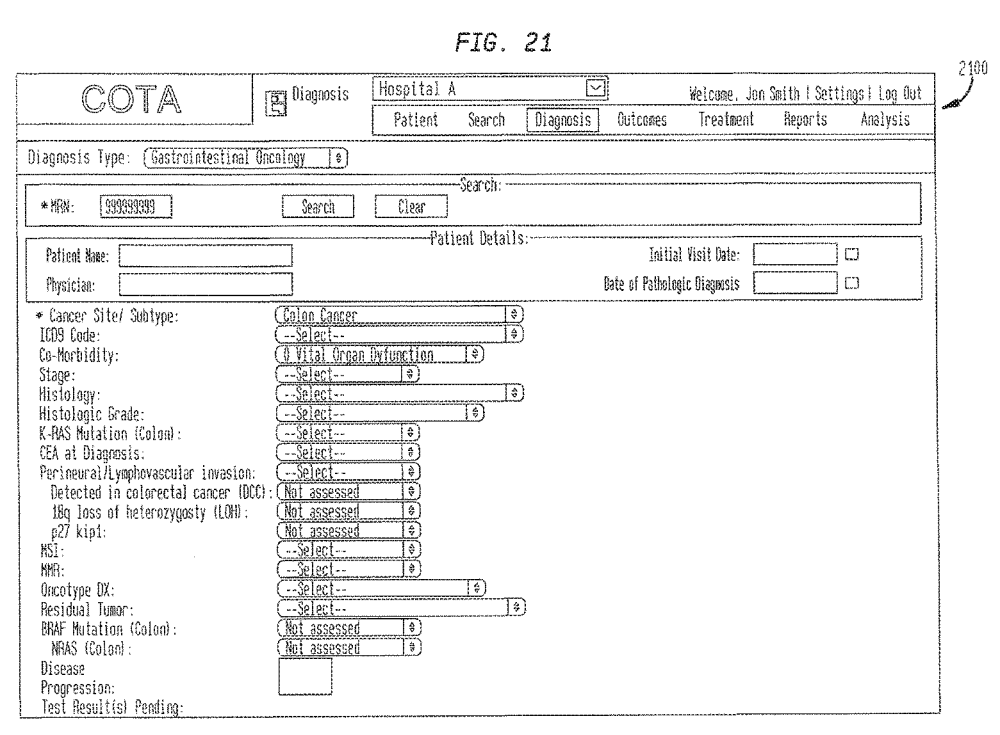
Figure 22:
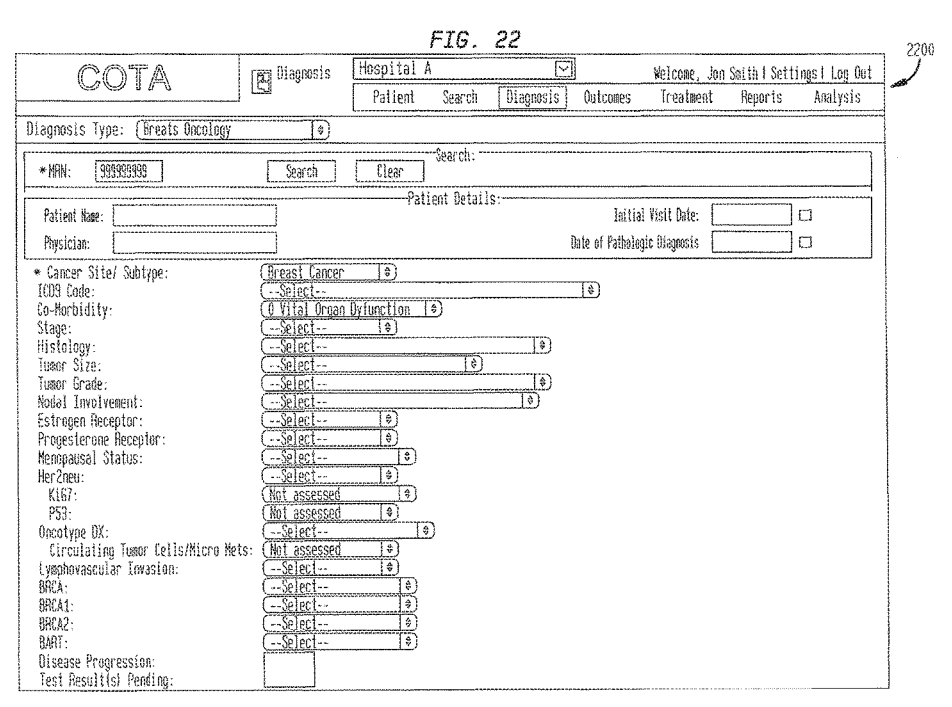
Figure 23:
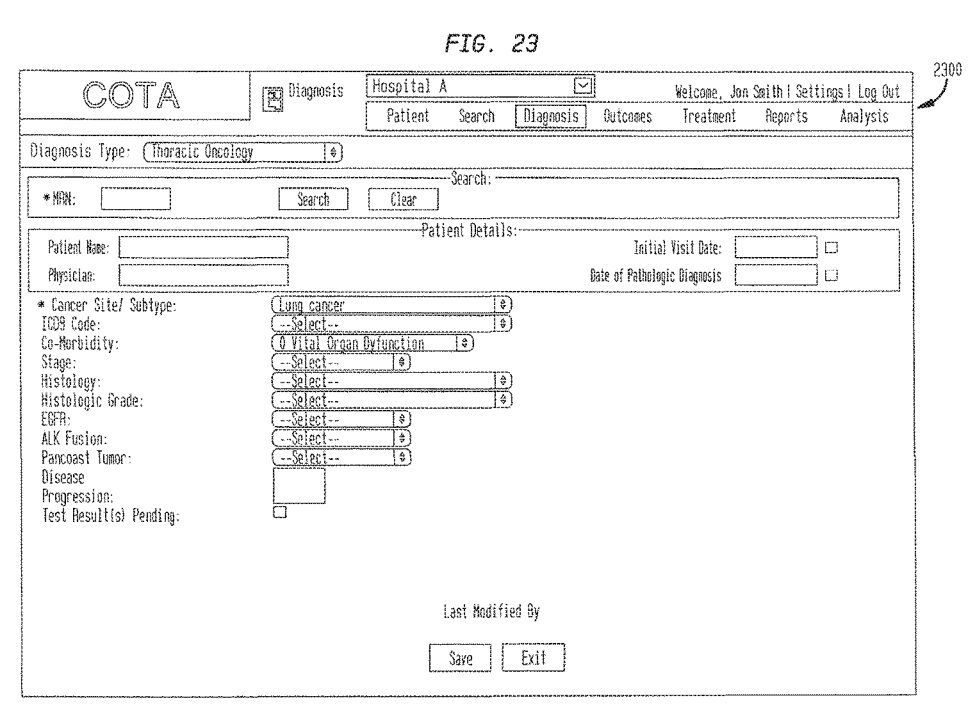

FIGS. 21-24 show graphical representations for different diagnosis types in accordance with one or more embodiments. FIG. 21 shows a diagnosis screen 2100 for gastrointestinal oncology (e.g., colon cancer). FIG. 22 shows a diagnosis screen 2200 for breast oncology (e.g., breast cancer). FIG. 23 shows a diagnosis screen 2300 for thoracic oncology (e.g., lung cancer). Diagnosis screens 2100, 2200, 2300 include a number of different parameters, such as tests or aspects of the disease. The parameters may be represented as simple indicators, numerically based parameters, standards based parameters, etc.

Figure 24:
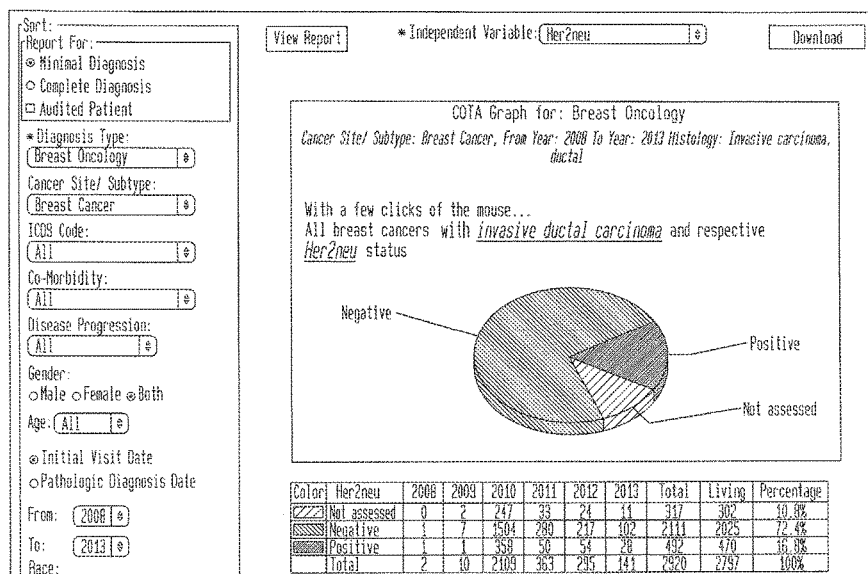
FIG. 24 shows a graphical representation illustrating the COTA module's data generation and sorting for breast oncology—breast cancer from year 2008 to year 2013 histology with invasive ductal carcinoma in accordance with an embodiment of the present disclosure.

FIG. 24 shows a graphical representation of a reporting screen 2400 illustrating the COTA module 220's data generation and sorting for breast oncology. Reporting screen 2400 shows breast cancer from year 2008 to year 2013 by histology, i.e., with invasive ductal carcinoma, in accordance with one embodiment. The reporting screen 2400 permits selection of breast cancer patients based on stage, age, progression, or any other parameter in real time. Advantageously, reporting screen 2400 allows categorization in a clinically relevant way.

Figure 25:
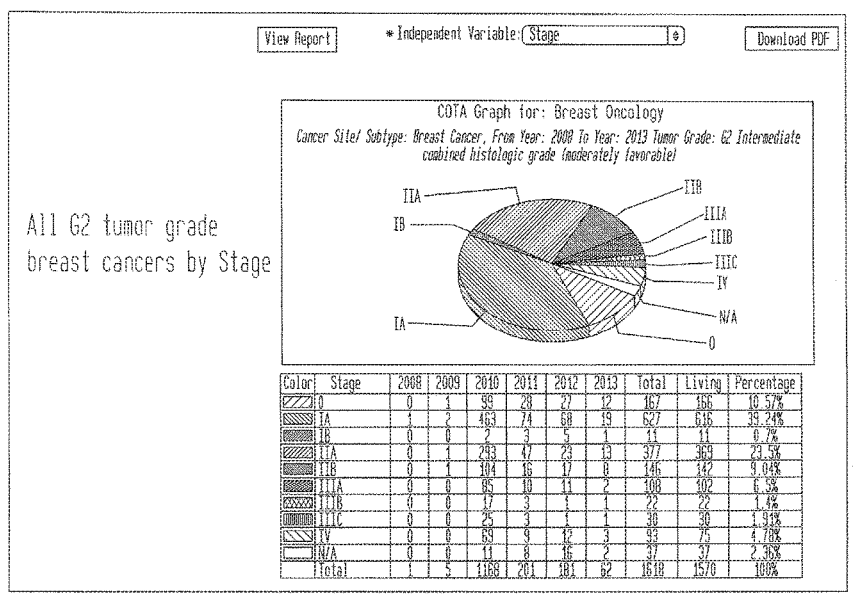
FIG. 25 shows a graphical representation illustrating the COTA module's data generation and sorting for breast oncology—breast cancer from year 2008 to year 2013 tumor grade and stage in accordance with an embodiment of the present disclosure.

FIG. 25 shows a graphical representation of a reporting screen 2500 illustrating the COTA module 220's data generation and sorting for breast oncology. Reporting screen 2500 shows all grade 2 breast cancer from year 2008 to year 2013 tumor by stage, in accordance with one embodiment.

Figure 26:
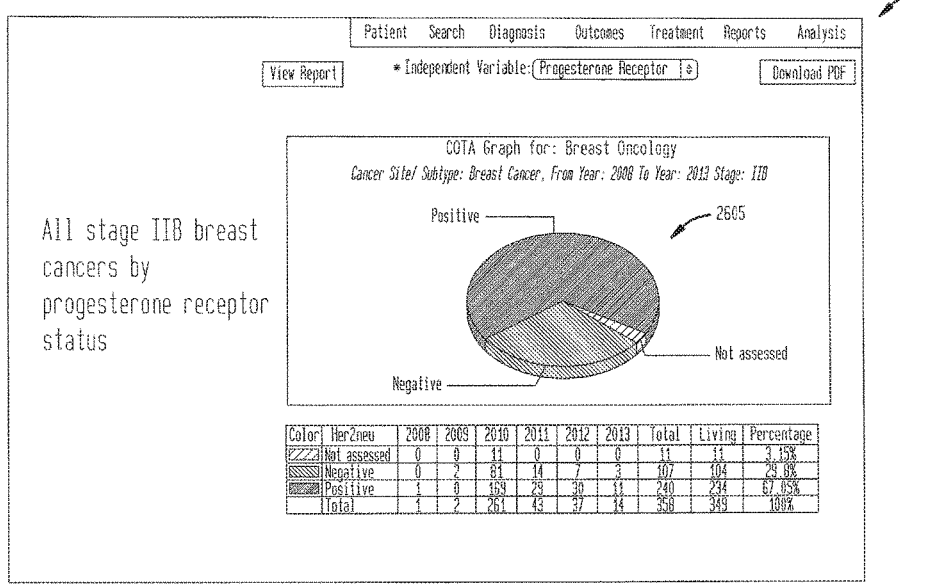
FIG. 26 shows a graphical representation illustrating the COTA module's data generation and sorting for breast cancer—stage IIB from year 2008 to 2013 in accordance with an embodiment of the present disclosure.

FIG. 26 shows a graphical representation of a reporting screen 2600 illustrating the COTA module 220's data generation and sorting for breast cancer. Reporting screen 2600 shows all stage IIB breast cancers from year 2008 to 2013, in accordance with one embodiment. Graph 2605 on reporting screen 2600 shows all stage IIB breast cancers by progesterone receptor status.

Figure 27:
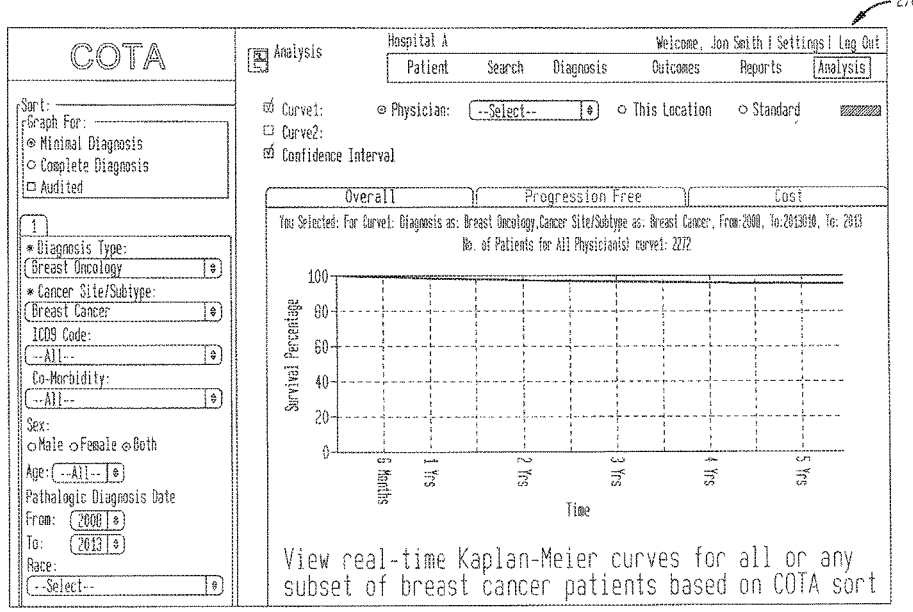
FIG. 27 shows a graphical representation illustrating overall survival outcomes for breast cancer patients in accordance with an embodiment of the present disclosure.
Figure 28:
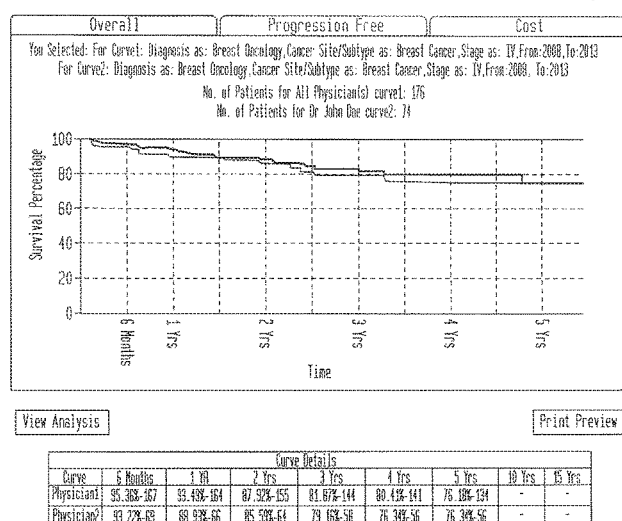
FIG. 28 shows a graphical representation illustrating outcomes for breast cancer—a comparison between two parties in accordance with an embodiment of the present disclosure.

FIG. 27 shows a graphical representation of an analysis screen 2700 illustrating overall survival outcomes for breast cancer patients in accordance with one embodiment. FIG. 28 shows a graphical representation 2800 illustrating survival outcomes for breast cancer as a comparison between Dr. John Doe (bold line) and the aggregate (non-bold line) parties, in accordance with one embodiment.

In one embodiment, the "node" described above represents every possible permutation of the variables shown in one or more of the graphical representations (e.g., in one or more of FIGS. 21-27).

Figure 29:
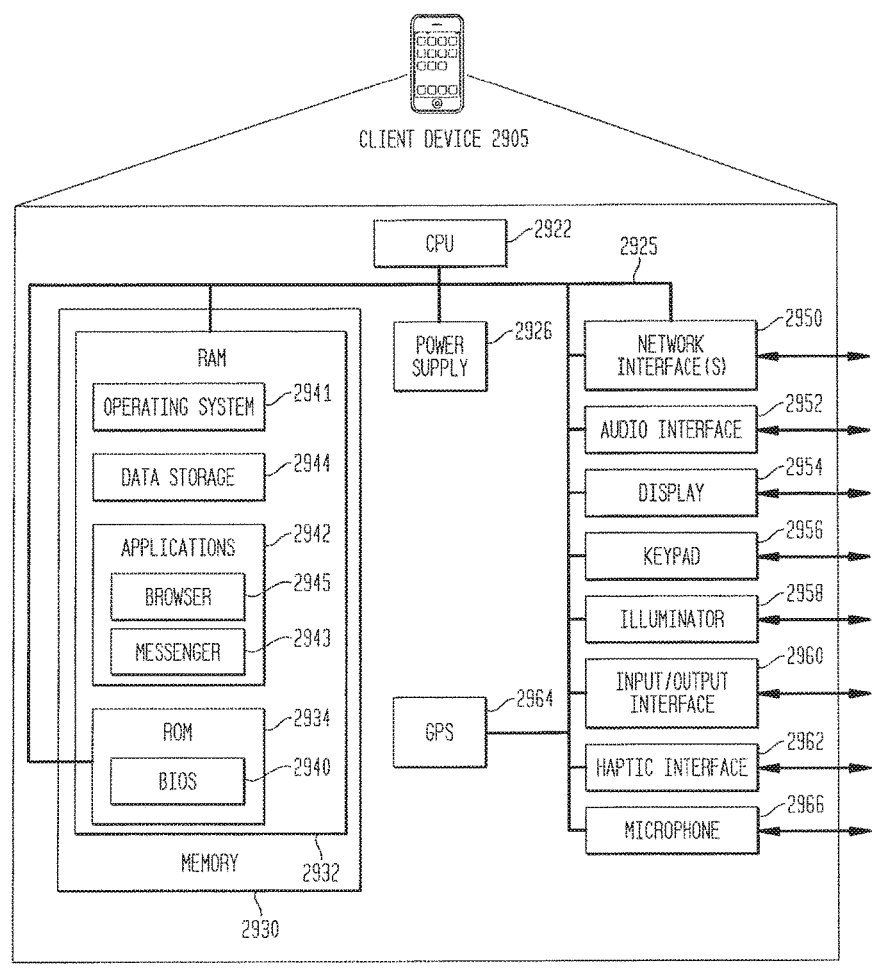
FIG. 29 depicts one example of a schematic diagram illustrating a client device in accordance with an embodiment of the present disclosure.

As shown in the example of FIG. 29, client device 2905 may include one or more processing units (also referred to herein as CPUs) 2922, which interface with at least one computer bus 2925. Client device 2905 may be, for example, user computer 210. A memory 2930 can be persistent storage and interfaces with the computer bus 2925. The memory 2930 includes RAM 2932 and ROM 2934. ROM 2934 includes a BIOS 2940. Memory 2930 interfaces with computer bus 2925 so as to provide information stored in memory 2930 to CPU 2922 during execution of software programs such as an operating system 2941, application programs 2942, device drivers, and software modules 2943, 2945 that comprise program code, and/or computer-executable process steps, incorporating functionality described herein, e.g., one or more of process flows described herein. CPU 2922 first loads computer-executable process steps from storage, e.g., memory 2932, data storage medium/media 2944, removable media drive, and/or other storage device. CPU 2922 can then execute the stored process steps in order to execute the loaded computer-executable process steps. Stored data, e.g., data stored by a storage device, can be accessed by CPU 2922 during the execution of computer-executable process steps.

Persistent storage medium/media 2944 is a computer readable storage medium(s) that can be used to store software and data, e.g., an operating system and one or more application programs. Persistent storage medium/media 2944 can also be used to store device drivers, such as one or more of a digital camera driver, monitor driver, printer driver, scanner driver, or other device drivers, web pages, content files, playlists and other files. Persistent storage medium/media 2206 can further include program modules and data files used to implement one or more embodiments of the present disclosure.

For the purposes of this disclosure a computer readable medium stores computer data, which data can include computer program code that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

Client device 2905 can also include one or more of a power supply 2926, network interface 2950, audio interface 2952, a display 2954 (e.g., a monitor or screen), keypad 2956, illuminator 2958, I/O interface 2960, a haptic interface 2962, a GPS 2964, a microphone 2966, a video camera, TV/radio tuner, audio/video capture card, sound card, analog audio input with A/D converter, modem, digital media input (HDMI, optical link), digital I/O ports (RS232, USB, FireWire, Thunderbolt), expansion slots (PCMCIA, ExpressCard, PCI, PCIe).

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium. Modules may be integral to one or more servers, or be loaded and executed by one or more servers. One or more modules may be grouped into an engine or an application.

Figure 30:
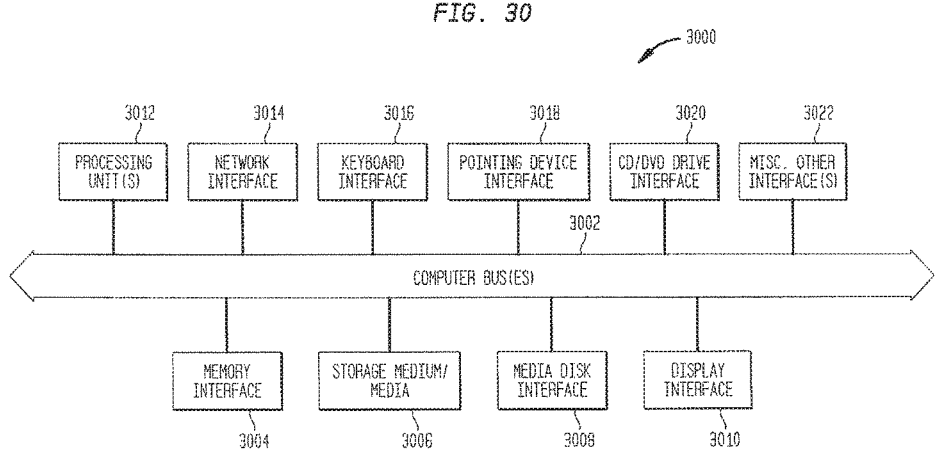
FIG. 30 is a block diagram illustrating an internal architecture of a computer in accordance with an embodiment of the present disclosure.

FIG. 30 is a block diagram illustrating an internal architecture of an example of a computer, such as server computer 205, user computer 210, and/or user computer 230, in accordance with one or more embodiments of the present disclosure. A computer as referred to herein refers to any device with a processor capable of executing logic or coded instructions, and could be a server, personal computer, set top box, tablet, smart phone, pad computer or media device, to name a few such devices. As shown in the example of FIG. 30, internal architecture 3000 includes one or more processing units (also referred to herein as CPUs) 3012, which interface with at least one computer bus 3002. Also interfacing with computer bus 3002 are persistent storage medium/media 3006, network interface 3014, memory 3004, e.g., random access memory (RAM), run-time transient memory, read only memory (ROM), etc., media disk drive interface 2308 as an interface for a drive that can read and/or write to media including removable media such as floppy, CD-ROM, DVD, etc. media, display interface 3010 as interface for a monitor or other display device, keyboard interface 3016 as interface for a keyboard, pointing device interface 3018 as an interface for a mouse or other pointing device, and miscellaneous other interfaces not shown individually, such as parallel and serial port interfaces, a universal serial bus (USB) interface, and the like.

Memory 3004 interfaces with computer bus 3002 so as to provide information stored in memory 3004 to CPU 3012 during execution of software programs such as an operating system, application programs, device drivers, and software modules that comprise program code, and/or computer-executable process steps, incorporating functionality described herein, e.g., one or more of process flows described herein. CPU 3012 first loads computer-executable process steps from storage, e.g., memory 3004, storage medium/media 3006, removable media drive, and/or other storage device. CPU 3012 can then execute the stored process steps in order to execute the loaded computer-executable process steps. Stored data, e.g., data stored by a storage device, can be accessed by CPU 3012 during the execution of computer-executable process steps.

As described above, persistent storage medium/media 3006 is a computer readable storage medium(s) that can be used to store software and data, e.g., an operating system and one or more application programs. Persistent storage medium/media 3006 can also be used to store device drivers, such as one or more of a digital camera driver, monitor driver, printer driver, scanner driver, or other device drivers, web pages, content files, playlists and other files. Persistent storage medium/media 3006 can further include program modules and data files used to implement one or more embodiments of the present disclosure.

Internal architecture 3000 of the computer can include (as stated above), a microphone, video camera, TV/radio tuner, audio/video capture card, sound card, analog audio input with A/D converter, modem, digital media input (HDMI, optical link), digital I/O ports (RS232, USB, FireWire, Thunderbolt), and/or expansion slots (PCMCIA, ExpressCard, PCI, PCIe).

CNA-guided care has two faces, which together, through the triad of a health care provider, a payer, and the patient suffering from a disease, enables value based care delivery in the United States through the application of CNAs.

The first face, the enabling tool, comprises interactions between a medical care provider, a computer containing a processor comprising a first COTA module, a first client device comprising a second COTA module that is communicatively linked to the first COTA via a network, and a payer. It enables a payer to transmit via the first client device comprising a second COTA module communicatively linked to the first COTA module of the processor, a communication over the network to the processor identifying a health care service under consideration for a patient whose health plan benefits cover the service; indicating that the service is for the purpose of diagnosing or treating a medical condition; and identifying variables selected by the payer. Upon receiving this communication from the payer, the first COTA module can transmit to the second COTA module information comprising (i) the clinical outcome data for each CNA, (ii) the adverse variance data for each medical provider at each CNA including both necessary care that is absent and unnecessary care contributing to the medical care provider's adverse variance for patients at each nodal address at key points in time during treatment; (iii) a cost report comprising cost data in real time for treating each patient in the patient population assigned to the CNA; and (iv) graphic analyses correlating one or more of (1) cost of care to clinical outcome; (2) incidence and severity of toxicity to cost of care and clinical outcome of care; and (3) therapy and quality of life. Based on this information, when the payer can establish at key points in time, (a) that the medical service is an appropriate delivery or level of service, considering potential benefits and harms to the patient; (b) that the medical service is effective in improving health outcome by improving clinical outcomes and reducing total cost of care; that the service is cost-effective for the medical condition being treated and the clinical outcome, compared to alternative health interventions or no intervention; and that the service follows generally accepted medical practice, the payer can approve payment to the medical care provider for the medical service for the patient.

Figure 31:
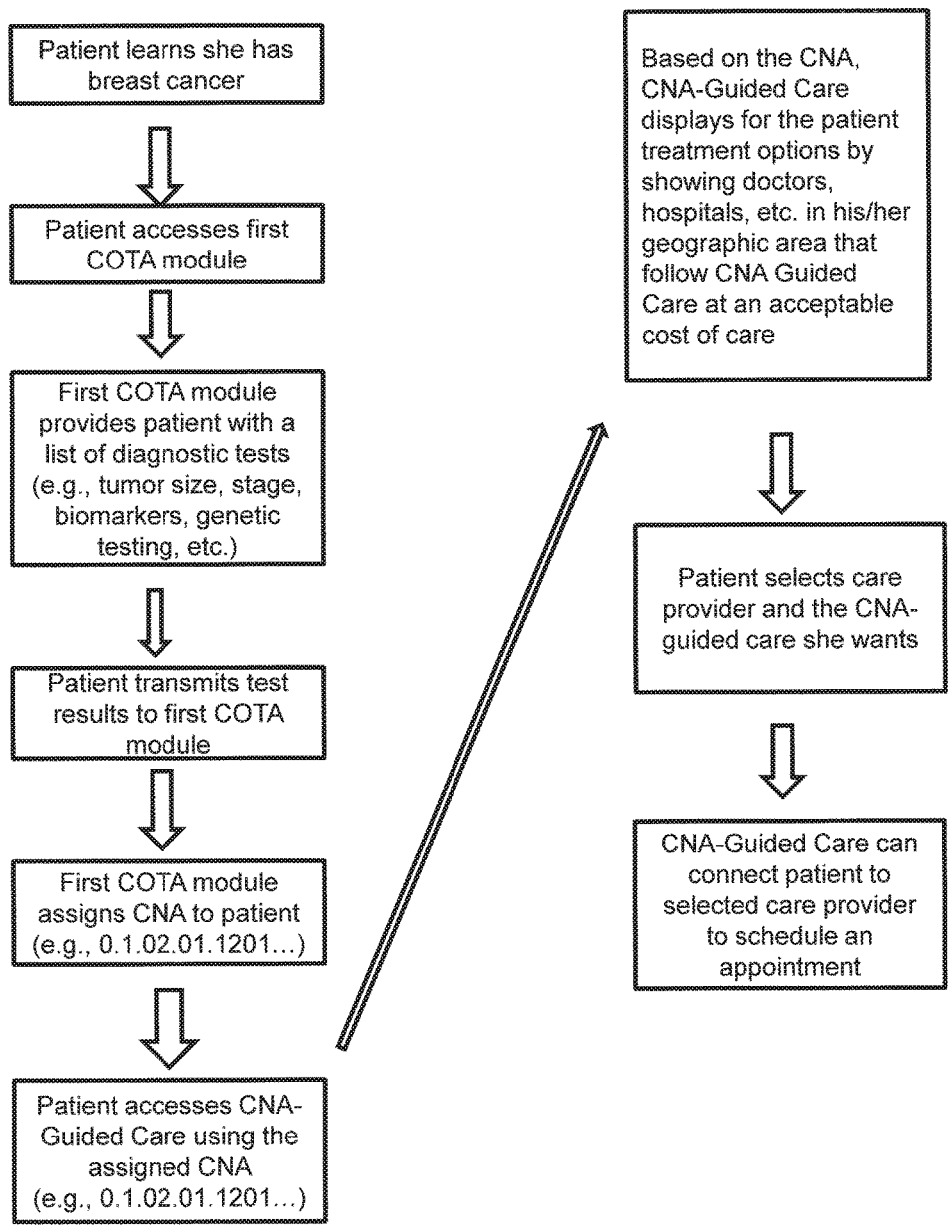
FIG. 31 is a flow chart showing the patient face of CNA-guided care in accordance with an embodiment of the present disclosure for a patient with breast cancer.
Figure 32:
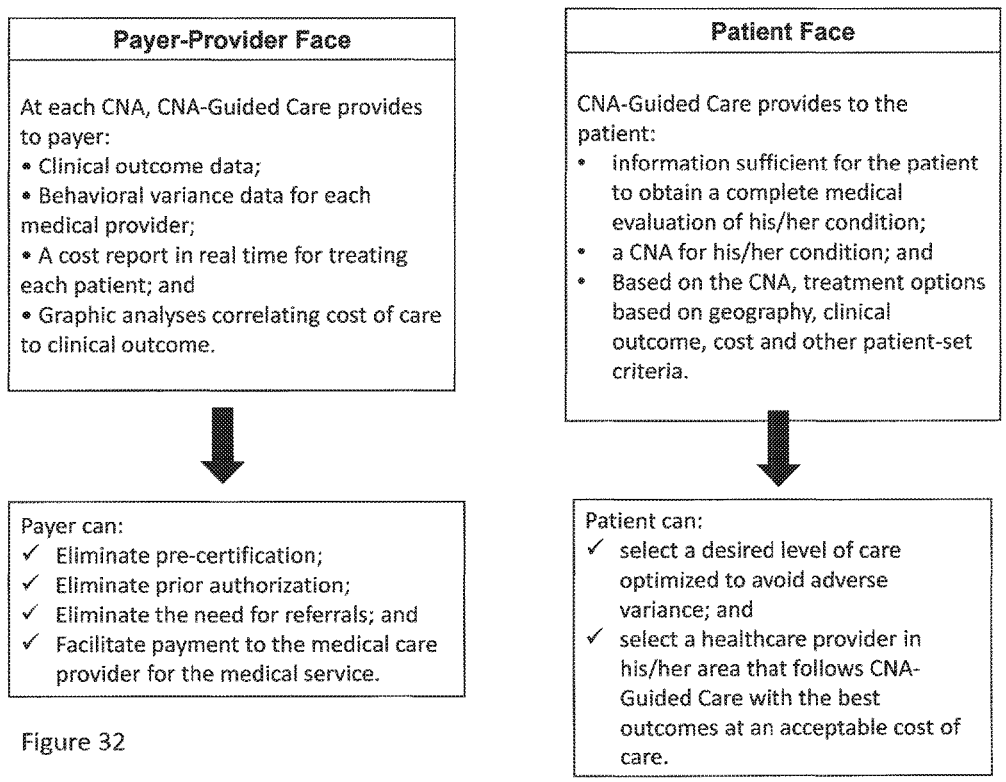
FIG. 32 is a block diagram illustrating the advantages of the two faces of CNA guided care. The provider-payer face enables elimination of precertification for testing, diagnostics, and therapeutic choices; elimination of prior authorization and the need for referrals optimizing fee for service based reimbursement and enabling a move from fee for service to risk-based reimbursement. The patient face for a patient using CNA guided care does three things: first, it provides information to the patient so the patient gets a complete evaluation of his/her condition (e.g., physical evaluation; laboratory evaluation; imaging, etc.) so that a CNA can be assigned; second, it shows the patient treatment options for the condition that optimize care and reduce risk of adverse variance; and third, it shows the patient the doctor's in his/her area who follow CNA guided care and have the best outcomes at an acceptable cost of care.

As depicted in the example in FIG. 31, the second face of CNA-guided healthcare in accordance with an embodiment of the present disclosure for a patient with breast cancer comprises interactions between the computer containing the processor comprising the first COTA module, a second client device comprising a third COTA module that is communicatively linked to the first COTA module via a network, and the patient. Upon exchanging a series of communications with the patient via the second client device comprising the third clinical outcome tracking and analysis module, the first COTA module does three things: it provides information to the patient so that the patient gets a complete medical evaluation of his/her condition (e.g., physical evaluation;

laboratory evaluation; imaging, etc.) so that a CNA can be assigned; using the assigned CNA it shows the patient treatment options for the condition that optimize care and reduce risk of adverse variance; and it shows the patient doctors in his/her geographic area who follow CNA-Guided Care and have the best outcomes at an acceptable cost of care so that the patient can select a health care provider and a desired level of CNA-guided care, As depicted in FIG. 32, from the payer's vantage point, the enabling tool can be effective to eliminate precertification for testing, diagnostics, and therapeutic choices; eliminate prior authorization; and eliminate the need for referrals. From the medical care provider's vantage point, it reduces the time necessary to pay the provider for healthcare. Accordingly, the enabling tool enables healthcare to optimize fee for service based reimbursement and to move from fee for services to risk-based care reimbursement (for example by bundling services), From the patient's vantage point, CNA-guided care does three things: first, it provides the patient with information sufficient for the patient to get a complete medical evaluation of his/her condition and for assigning a CNA to the patient; second, using the CNA, it shows the patient treatment options based on geography, clinical outcome, cost and other patient-set criteria, which enables the patient to select care optimized to avoid adverse variance; third it shows the patient health care providers in his/her area who follow CNA guided care that have the best outcomes at an acceptable cost of care.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the user computing device or server or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

While the system and method have been described in terms of one or more embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

What is claimed is:

1. A method for improving clinical outcomes at a specific patient level and for decreasing total cost of care at a population level comprising:
a computer containing a processor comprising a first clinical outcome tracking and analysis module executing on the processor comprising the first clinical outcome tracking and analysis module steps comprising:
(a) accounting for biological variance upfront by grouping patients in a patient population, thereby effectively removing biological variance as a factor in value of care, and leaving treatment variance as a predominant factor in treatment outcome by:
  (i) receiving, collecting and recording in a database personal health information from each patient in the patient population, the personal health information comprising each parameter that characterizes each patient in the patient population and information that impacts survival, prognosis, or treatment based on the latest scientific knowledge or medical guidelines;
  (ii) sorting the personal health information for each patient in the patient population using a sorting filter to provide a sorted set of personal health information for that population, and to identify patients satisfying each parameter in the patient population;
  (iii) classifying like personal health information, and grouping types of patients in the patient population based on the personal health information associated with the patient population by generating and assigning a plurality of Clinical outcome tracking and analysis Nodal Addresses (CNAs) within the first clinical outcome tracking and analysis module, wherein said generating and assigning said plurality of nodal addresses comprises:
    (1) representing each CNA as a discrete punctuated string of digits comprising a prefix, a middle and a suffix that represent a set of preselected variables that partition the sorted and classified information into a clinically relevant set of health information;
    (2) reducing trillions of possible permutations to a reduced number of clinically meaningful permutations based on the discrete punctuated string of digits representing each CNA that enable analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost;
    (3) reducing processing requirements and time for processing to make real-time monitoring of medical provider performance efficient based on the discrete punctuated string of digits representing each CNA and based on the reduction in permutations; and
    (4) enabling prediction of key points in time at which behavioral variance is likely to occur and interrupting treatment flow to avoid over-/under-utilization of care to prevent the behavioral variance;
  (iv) measuring clinical outcome for each CNA by: analyzing the clinically relevant set of personal health information for the subset of the patient population for one or more patients in the subset of the patient population; and (v) measuring behavioral variance for each medical care provider of each patient in the patient population assigned to each CNA by comparing differences between one medical care provider and another medical care provider in treating, testing, following up, complying with prescribed medicines, and cost for each patient in the patient population assigned to each CNA;

(b) upon receiving communications from a payer via a first client device comprising a second clinical outcome tracking and analysis module, identifying a health care service under consideration for a patient whose health plan benefits cover the medical service and variables selected by the payer, the first clinical outcome tracking and analysis module transmitting to the second clinical outcome tracking and analysis module information comprising, (1') the clinical outcome data for each CNA in (iv), (2') the behavioral variance data for each medical provider at each CNA in (v);

(3') a cost report comprising cost data in real time for treating each patient in the patient population assigned to the CNA in (iii); and (4') one or more graphic analyses correlating cost of care to clinical outcome;

wherein the information is sufficient for the payer to establish at the key points in time, (a') that the medical service is an appropriate delivery or level of service, considering potential benefits and harms to the patient;

(b') that the medical service is effective in improving health outcome by improving clinical outcomes and reducing total cost of care;

(c') that the service is cost-effective for the medical condition being treated and the clinical outcome, compared to alternative health interventions or no intervention; and (d') that the service follows generally accepted medical practice, and for the payer to approve payment to the medical care provider for the medical service;

(c) upon exchanging a series of communications with the patient via a second client device comprising a third clinical outcome tracking and analysis module, the first clinical outcome tracking and analysis module providing information sufficient for a complete medical evaluation of the patient and for assigning a CNA to the patient, and using the CNA to determine an optimal level of care with a reduced risk of adverse variance; and to select a health care provider and a desired level of CNA-guided care, the series of communications comprising:

(i") in response to a first communication from the patient reporting a health concern to the processor of the computer server comprising the first clinical outcome tracking and analysis module, sending to the second client device comprising the third clinical outcome tracking and analysis module in reply a second communication containing list of tests needed to diagnose the health concern as a medical condition;

(ii") in response to a third communication from the patient containing results of the tests needed to diagnose the health concern in (i"), sending to the second client device comprising the third clinical outcome and analysis module in reply a fourth communication containing a diagnosis of the medical condition and a list of additional tests needed for further classifying the medical condition;

(iii") in response to a fifth communication from the patient containing the results of the additional tests in (i"), based on the results of the tests, the diagnosis in (ii"), and the list of additional tests in (ii"), (a") assigning, a CNA to the patient from the plurality of CNAs available in a(iii), the assigned CNA containing the clinically relevant set of health information for the patient; and (b") transmitting to the second client device comprising the third clinical outcome tracking module a sixth communication comprising:

(1") the assigned CNA; and (2") a geographically organized list of medical professionals treating patients within the assigned CNA, wherein the list of medical professionals is classified by one or more of geography, clinical outcome or cost;

(iv") in response to a seventh communication from the patient selecting an optimal care plan comprising a reduced risk of adverse variance and a medical professional that meets at least one or more of geographical, cost, and outcome needs of the patient, communicatively linking to a computing device comprising a third clinical outcome tracking and analysis module at the selected medical professional's office to facilitate scheduling of an appointment of the patient with the selected medical professional wherein the processor comprising the first clinical outcome tracking and analysis module, the first client device comprising a second clinical outcome tracking and analysis module, the second client device comprising a second clinical outcome tracking and analysis module, and the computing device comprising the third clinical outcome tracking and analysis module are communicatively linked via a network.

2. The method as recited in claim 1, wherein (a) the parameters of sorting in (a)(ii) comprise one or more of: sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers, and cost of care; or (b) the set of preselected variables in (a)(iii)(1) includes a disease-specific clinical molecular phenotype, wherein the string of digits representing the phenotype is determined based on a directed graph; or (c) the key points in time in step (a)(iii)(4) and step (b)(4') include one or more of at diagnosis, at progression, at dose change; at drug change; upon toxicity, and trending towards variance from desired outcome; or (d) the correlating cost of care to clinical outcome step in (b)(4') comprises correlating one or more of incidence of toxicity, severity of toxicity; therapy; and quality of life to cost of care and outcome of care; or (e) the receiving of the transmission from the client device in (b) or (c) is via a human user or a technical process; or (f) the assigned CNA in (c)(iii")(b")(1") is associated with one or more bundles of predetermined patient care services for treatment of the condition; or (g) the clinical outcome in (c)(iii")(b")(2") comprises one or more of: therapeutic agent received, delivered dose intensity, dose interval, dose duration, quality of life metrics, toxicity to therapy, progression free survival, overall survival, response metrics, and death; or (h) the list of medical professionals in step (c)(iii")(b")(2") is visually classified by clinical outcome.

3. The method as recited in claim 2, wherein the one or more bundles of predetermined patient care services provides a predetermined course of treatment, cost certainty for treatment of the condition, or both.

4. The method as recited in claim 2, further comprising identifying the best clinical outcome at the lowest cost of care at the CNA by ranking both clinical outcome and cost of care in the one or more bundles of predetermined patient care services.

5. The method as recited in claim 2 wherein in (h), the visual classification of the list of medical professionals by clinical outcome comprises:
   (a) green signifying a better than average clinical outcome;
   (b) yellow signifying an average clinical outcome; and
   (c) red signifying a poorer than average clinical outcome.

6. The method as recited in claim 1, further comprising, with permission from the patient and the selected medical professional:
   transmitting the personal health information of the patient from the first clinical outcome tracking and analysis module, to a computing device comprising a fourth clinical outcome tracking and analysis module at the selected medical professional's office.

7. The method as recited in claim 1, wherein in step (d)(2), the behavioral variance data for each medical provider at each CNA in (c) includes both necessary care that is absent and unnecessary care contributing to the medical care provider's adverse variance for patients at each CNA at the key points in time during treatment.

8. The method as recited in claim 1, step (d) further comprising indicating that the service is for the purpose of diagnosing or treating a medical condition.

9. The method as recited in claim 1, wherein in step (b)(3'), the cost report contains:
   a comparison between physician and average cost per revenue; or
   hospital contribution margin in dollars and percent comparisons; or
   hospital average revenue per patient; or
   hospital average cost per patient; or
   average cost per case for each physician, weight peer average; or
   average cost of imaging, lab work, evaluation and management; or
   pharmaceuticals, medical supplies and other expenses for each physician; or
   a combination thereof.

10. The method as recited in claim 1, wherein in step (b), the variables selected by the payer include variables that identify certain attributes of the personal health information as a desired set of characteristics; one or more attributes added by the payer to the personal health information to identify the personal health information of each patient as being on an equal level of importance to other health information in the patient population database, or both.

11. A system for improving clinical outcomes at a specific patient level and for decreasing total cost of care at a population level comprising:
   (A) a processor of a computer server comprising:
      a database comprising personal health information and data for a population of human subjects;
      a first clinical outcome tracking and analysis module communicatively linked to the database and a network; and
      a memory to store computer program instructions;
   (B) a first client device comprising a processing unit; a memory, and a second clinical outcome tracking and analysis module communicatively linked to the first clinical outcome tracking and analysis module of the processor of the computer server; and
   (C) a second client device comprising a processing unit, a memory, and a third clinical outcome tracking and analysis module communicatively linked to the first clinical outcome tracking and analysis module of the processor of the computer server;
   the computer program instructions of (A), when executed on the processor causing the first clinical outcome tracking and analysis module to perform operations comprising:
      (a) accounting for biological variance upfront by grouping patients in a patient population, thereby effectively removing biological variance as a factor in value of care, and leaving treatment variance as a predominant factor in treatment outcome by:
         (i) receiving, collecting and recording in a database personal health information from each patient in the patient population, the personal health information comprising each parameter that characterizes each patient in the patient population and information that impacts survival, prognosis, or treatment based on the latest scientific knowledge or medical guidelines;
         (ii) sorting the personal health information for each patient in the patient population using a sorting filter to provide a sorted set of personal health information for that population, and to identify patients satisfying each parameter in the patient population;
         (iii) classifying like personal health information, and grouping types of patients in the patient population based on the personal health information associated with the patient population by generating and assigning a plurality of Clinical outcome tracking and analysis Nodal Addresses (CNAs) within the first clinical outcome tracking and analysis module, wherein said generating and assigning said plurality of CNAs comprises:
            (1) representing each CNA as a discrete punctuated string of digits comprising a prefix, a middle and a suffix that represent a set of preselected variables that partition the sorted and classified information into a clinically relevant set of health information;
            (2) reducing trillions of possible permutations to a reduced number of clinically meaningful permutations based on the discrete punctuated string of digits representing each CNA that enable analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost;
            (3) reducing processing requirements and time for processing to make real-time monitoring of medical provider performance efficient based on the discrete punctuated string of digits representing each CNA and based on the reduction in permutations; and (4) enabling prediction of key points in time at which behavioral variance is likely to occur and interrupting treatment flow to avoid over-/under-utilization of care to prevent the behavioral variance;

(iv) measuring clinical outcome for each CNA by:
analyzing the clinically relevant set of personal health information for the subset of the patient population for one or more patients in the subset of the patient population; and (v) measuring behavioral variance for each medical care provider of each patient in the patient population assigned to each CNA by comparing differences between one medical care provider and another medical care provider in treating, testing, following up, complying with prescribed medicines, and cost for each patient in the patient population assigned to each CNA;

(b) upon receiving communications from the payer via the first client device comprising the second clinical outcome tracking and analysis module, identifying a health care service under consideration for the patient whose health plan benefits cover the medical service and variables selected by the payer, transmitting to the second clinical outcome tracking and analysis module information comprising:

(1') the clinical outcome data for each CNA in (iv);
(2') the behavioral variance data for each medical provider at each CNA in (v);
(3') a cost report comprising cost data in real time for treating each patient in the patient population assigned to the CNA in (iii); and
(4') one or more graphic analyses correlating cost of care to clinical outcome;

wherein the information is sufficient
for the payer to establish at the key points in time,
(a') that the medical service is an appropriate delivery or level of service, considering potential benefits and harms to the patient;
(b') that the medical service is effective in improving health outcome by improving clinical outcomes and reducing total cost of care;
(c') that the service is cost-effective for the medical condition being treated and the clinical outcome, compared to alternative health interventions or no intervention; and
(d') that the service follows generally accepted medical practice, and for the payer to approve payment to the medical care provider for the medical service;

(c) upon exchanging a series of communications with the patient via the second client device comprising the third clinical outcome tracking and analysis module,
providing information sufficient for a complete medical evaluation of the patient and for assigning a CNA to the patient, and
using the CNA to determine an optimal level of care with a reduced risk of adverse variance; and to select a health care provider and a desired level of CNA-guided care,
the series of communications comprising:
(i") in response to a first communication from the patient reporting a health concern to the processor of the computer server comprising the first clinical outcome tracking and analysis module,
sending to the second client device comprising the third clinical outcome tracking and analysis module in reply a second communication containing list of tests needed to diagnose the health concern as a medical condition;

(ii") in response to a third communication from the patient containing results of the tests needed to diagnose the health concern in (i"),
sending to the second client device comprising the third clinical outcome and analysis module in reply a fourth communication containing a diagnosis of the medical condition and a list of additional tests needed for further classifying the medical condition;

(iii") in response to a fifth communication from the patient containing the results of the additional tests in (i"), based on the results of the tests, the diagnosis in (ii"), and the list of additional tests in (ii"),
(a") assigning, a CNA to the patient from the plurality of CNAs available in a(iii), the assigned CNA containing the clinically relevant set of health information for the patient; and
(b") transmitting to the second client device comprising the third clinical outcome tracking module a sixth communication comprising:
(1") the assigned CNA; and
(2") a geographically organized list of medical professionals treating patients within the assigned CNA, wherein the list of medical professionals is classified by one or more of geography, clinical outcome or cost;

(iv") in response to a seventh communication from the patient selecting an optimal care plan with a reduced risk of adverse variance and a medical professional that meets at least one or more of geographical, cost, and outcome needs of the patient, communicatively linking to a computing device comprising a third clinical outcome tracking and analysis module at the selected medical professional's office to facilitate the scheduling of an appointment of the patient with the selected medical professional.

12. The system as recited in claim 11, wherein
(a) the parameters of sorting in (a)(ii) comprise one or more of: sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers, and cost of care; or
(b) the set of preselected variables in (a)(iii)(1) includes a disease-specific clinical molecular phenotype, wherein the string of digits representing the phenotype is determined based on a directed graph; or
(c) the key points in time in step (a)(iii)(4) and step (b)(4') include one or more of at diagnosis, at progression, at dose change; at drug change; upon toxicity, and trending towards variance from desired outcome; or
(d) the correlating cost of care to clinical outcome step in (b)(4') comprises correlating one or more of incidence of toxicity, severity of toxicity; therapy; and quality of life to cost of care and outcome of care; or
(e) the receiving of the transmission from the client device in (b) or (c) is via a human user or a technical process; or (f) the assigned CNA in (c)(iii")(b")(1") is associated with one or more bundles of predetermined patient care services for treatment of the condition; or (g) the clinical outcome in (c)(iii")(b")(2") comprises one or more of: therapeutic agent received, delivered dose intensity, dose interval, dose duration, quality of life metrics, toxicity to therapy, progression free survival, overall survival, response metrics, and death; or (h) the list of medical professionals in step (c)(iii")(b") (2") is visually classified by clinical outcome.

13. The system as recited in claim 12, wherein the one or more bundles of predetermined patient care services provides a predetermined course of treatment, cost certainty for treatment of the condition, or both.

14. The system as recited in claim 12, further comprising identifying the best clinical outcome at the lowest cost of care at the assigned CNA by ranking both clinical outcome and cost of care in the one or more bundles of predetermined patient care services.

15. The system as recited in claim 12 wherein in (h), the visual classification of the list of medical professionals by clinical outcome comprises:
    (a) green signifying a better than average clinical outcome;
    (b) yellow signifying an average clinical outcome; and
    (c) red signifying a poorer than average clinical outcome.

16. The system as recited in claim 11, further comprising, with permission from the patient and the selected medical professional:
    transmitting the personal health information of the patient from the first clinical outcome tracking and analysis module, to a computing device comprising a fourth clinical outcome tracking and analysis module at the selected medical professional's office.

17. The system as recited in claim 11, wherein in step (b)(2), the behavioral variance data for each medical provider at each CNA in (c) includes both necessary care that is absent and unnecessary care contributing to the medical care provider's adverse variance for patients at each CNA at the key points in time during treatment.

18. The system as recited in claim 11, further comprising (d) indicating that the service is for the purpose of diagnosing or treating a medical condition.

19. The system as recited in claim 11, wherein in step (b)(3), the cost report contains:
    a comparison between physician and average cost per revenue; or
    hospital contribution margin in dollars and percent comparisons; or
    hospital average revenue per patient; or
    hospital average cost per patient; or
    average cost per case for each physician, weight peer average; or
    average cost of imaging, lab work, evaluation and management; or
    pharmaceuticals, medical supplies and other expenses for each physician; or
    a combination thereof.

20. The system as recited in claim 11, wherein in step (b), the variables selected by the payer include variables that identify certain attributes of the personal health information as a desired set of characteristics; one or more attributes added by the payer to the personal health information to identify the personal health information of each patient as being on an equal level of importance to other health information in the patient population database, or both.

21. A non-transitory computer readable medium storing computer program instructions for facilitating interactions (A) between a medical care provider, a computer containing a processor comprising a first clinical outcome tracking and analysis module, a first client device comprising a second clinical outcome tracking and analysis module communicatively linked to the first clinical outcome tracking and analysis module via a network, and a payer, and (B) between the computer containing the processor comprising a first clinical outcome tracking and analysis module, a second client device comprising a third clinical outcome tracking and analysis module communicatively linked to the first clinical outcome tracking and analysis module via the network, and a patient, which, when executed on the processor comprising the first clinical outcome tracking and analysis module, causes the first clinical outcome and tracking module to perform operations comprising:
    (a) accounting for biological variance upfront by grouping patients in a patient population, thereby effectively removing biological variance as a factor in value of care, and leaving treatment variance as a predominant factor in treatment outcome by:
        (i) receiving, collecting and recording in a database personal health information from each patient in the patient population, the personal health information comprising each parameter that characterizes each patient in the patient population and information that impacts survival, prognosis, or treatment based on the latest scientific knowledge or medical guidelines;
        (ii) sorting the personal health information for each patient in the patient population using a sorting filter to provide a sorted set of personal health information for that population, and to identify patients satisfying each parameter in the patient population;
        (iii) classifying like personal health information, and grouping types of patients in the patient population based on the personal health information associated with the patient population by generating and assigning a plurality of Clinical outcome tracking and analysis Nodal Addresses (CNAs) within the first clinical outcome tracking and analysis module, wherein said generating and assigning said plurality of nodal addresses comprises:
            (1) representing each CNA as a discrete punctuated string of digits comprising a prefix, a middle and a suffix that represent a set of preselected variables that partition the sorted and classified information into a clinically relevant set of health information;
            (2) reducing trillions of possible permutations to a reduced number of clinically meaningful permutations based on the discrete punctuated string of digits representing each CNA that enable analysis of first behavioral and then consequent clinical and cost outcome variance from an ideal value, expressed as best clinical outcome at lowest possible cost, in a requisite time needed to alert for necessary care and avoidance of unnecessary care, thereby increasing the value of care, meaning better clinical outcomes at a lowest possible cost;
            (3) reducing processing requirements and time for processing to make real-time monitoring of medical provider performance efficient based on the discrete punctuated string of digits representing each CNA and based on the reduction in permutations; and
            (4) enabling prediction of key points in time at which behavioral variance is likely to occur and interrupting treatment flow to avoid over-/under-utilization of care to prevent the behavioral variance;
(iv) measuring clinical outcome for each nodal address by:
analyzing the clinically relevant set of personal health information for the subset of the patient population for one or more patients in the subset of the patient population; and
(v) measuring behavioral variance for each medical care provider of each patient in the patient population assigned to each CNA by comparing differences between one medical care provider and another medical care provider in treating, testing, following up, complying with prescribed medicines, and cost for each patient in the patient population assigned to each CNA;
(b) upon receiving communications from the payer via the first client device comprising the second clinical outcome tracking and analysis module, identifying a health care service under consideration for the patient whose health plan benefits cover the medical service and variables selected by the payer, transmitting to the second clinical outcome tracking and analysis module information comprising:
(1') the clinical outcome data for each CNA in (iv);
(2') the behavioral variance data for each medical provider at each CNA in (v);
(3') a cost report comprising cost data in real time for treating each patient in the patient population assigned to the CNA in (iii); and
(4') one or more graphic analyses correlating cost of care to clinical outcome;
wherein the information is sufficient
for the payer to establish at the key points in time,
(a') that the medical service is an appropriate delivery or level of service, considering potential benefits and harms to the patient;
(b') that the medical service is effective in improving health outcome by improving clinical outcomes and reducing total cost of care;
(c') that the service is cost-effective for the medical condition being treated and the clinical outcome, compared to alternative health interventions or no intervention; and
(d') that the service follows generally accepted medical practice, and
for the payer to approve payment to the medical care provider for the medical service;
(c) upon exchanging a series of communications with the patient via the second client device comprising the third clinical outcome tracking and analysis module,
providing information sufficient for a complete medical evaluation of the patient and for assigning a CNA to the patient, and
using the CNA to determine an optimal level of care with a reduced risk of adverse variance; and to select a health care provider and a desired level of CNA-guided care,
the series of communications comprising:
(i") in response to a first communication from the patient reporting a health concern to the processor of the computer server comprising the first clinical outcome tracking and analysis module,
sending to the second client device comprising the third clinical outcome tracking and analysis module in reply a second communication containing list of tests needed to diagnose the health concern as a medical condition;
(ii") in response to a third communication from the patient containing results of the tests needed to diagnose the health concern in (i"),
sending to the second client device comprising the third clinical outcome and analysis module in reply a fourth communication containing a diagnosis of the medical condition and a list of additional tests needed for further classifying the medical condition;
(iii") in response to a fifth communication from the patient containing the results of the additional tests in (i"), based on the results of the tests, the diagnosis in (ii"), and the list of additional tests in (ii"):
(a") assigning, a CNA to the patient from the plurality of CNAs available in a(iii), the assigned CNA containing the clinically relevant set of health information for the patient; and
(b") transmitting to the second client device comprising the third clinical outcome tracking module a sixth communication comprising:
(1") the assigned CNA; and
(2") a geographically organized list of medical professionals treating patients within the assigned nodal address, wherein the list of medical professionals is classified by one or more of geography, clinical outcome or cost;
(iv") in response to a seventh communication from the patient selecting an optimal care plan with a reduced risk of adverse variance and a medical professional that meets at least one or more of geographical, cost, and outcome needs of the patient
communicatively linking to a computing device comprising a third clinical outcome tracking and analysis module at the selected medical professional's office to facilitate the scheduling of an appointment of the patient with the selected medical professional.

22. The non-transitory computer readable medium as recited in claim 21, wherein
(a) the parameters of sorting in (a)(ii) comprise one or more of: sex, age, ethnicity, comorbidities, tobacco use, source of insurance, medical record number, primary care physician, referring physician, hospital, approved service vendors, disease-specific clinical molecular phenotype, therapy intent, stage of therapy, biomarkers, and cost of care; or
(b) the set of preselected variables in (a)(iii)(1) includes a disease-specific clinical molecular phenotype, wherein the string of digits representing the phenotype is determined based on a directed graph; or
(c) the key points in time in step (a)(iii)(4) and step (b)(4') include one or more of at diagnosis, at progression, at dose change; at drug change; upon toxicity, and trending towards variance from desired outcome; or
(d) the correlating cost of care to clinical outcome step in (b)(4') comprises correlating one or more of incidence of toxicity, severity of toxicity; therapy; and quality of life to cost of care and outcome of care; or
(e) the receiving of the transmission from the client device in (b) or (c) is via a human user or a technical process; or
(f) the assigned CNA in (c)(iii")(b")(1") is associated with one or more bundles of predetermined patient care services for treatment of the condition; or (g) the clinical outcome in (c)(iii")(b")(2") comprises one or more of: therapeutic agent received, delivered dose intensity, dose interval, dose duration, quality of life metrics, toxicity to therapy, progression free survival, overall survival, response metrics, and death; or (h) the list of medical professionals in step (c)(iii")(b")(2") is visually classified by clinical outcome.

23. The non-transitory computer readable medium as recited in claim 22, wherein the one or more bundles of predetermined patient care services provides a predetermined course of treatment, cost certainty for treatment of the condition, or both.

24. The non-transitory computer readable medium as recited in claim 22, further comprising identifying the best clinical outcome at the lowest cost of care at the assigned CNA by ranking both clinical outcome and cost of care in the one or more bundles of predetermined patient care services.

25. The non-transitory computer readable medium as recited in claim 22 wherein in (h), the visual classification of the list of medical professionals by clinical outcome comprises:

(a) green signifying a better than average clinical outcome;

(b) yellow signifying an average clinical outcome; and (c) red signifying a poorer than average clinical outcome.

26. The non-transitory computer readable medium as recited in claim 21, further comprising, with permission from the patient and the selected medical professional:

transmitting the personal health information of the patient from the first clinical outcome tracking and analysis module, to a computing device comprising a fourth clinical outcome tracking and analysis module at the selected medical professional's office.

27. The non-transitory computer readable medium as recited in claim 21, wherein in step (b)(2), the behavioral variance data for each medical provider at each CNA in (c) includes both necessary care that is absent and unnecessary care contributing to the medical care provider's adverse variance for patients at each CNA at the key points in time during treatment.

28. The non-transitory computer readable medium as recited in claim 21, further comprising (d) indicating that the service is for the purpose of diagnosing or treating a medical condition.

29. The non-transitory computer readable medium as recited in claim 21, wherein in step (b)(3), the cost report contains:

a comparison between physician and average cost per revenue; or hospital contribution margin in dollars and percent comparisons; or hospital average revenue per patient; or hospital average cost per patient; or average cost per case for each physician, weight peer average; or average cost of imaging, lab work, evaluation and management; or pharmaceuticals, medical supplies and other expenses for each physician; or a combination thereof.

30. The non-transitory computer readable medium according to claim 21, wherein in step (b), the variables selected by the payer include variables that identify certain attributes of the personal health information as a desired set of characteristics; one or more attributes added by the payer to the personal health information to identify the personal health information of each patient as being on an equal level of importance to other health information in the patient population database, or both.

* * * * *